(12) United States Patent
Kmak et al.

(10) Patent No.: US 12,357,204 B2
(45) Date of Patent: Jul. 15, 2025

(54) MEDICAL DEVICE AND SHEATH SEAL AND SEAL VERIFICATION

(71) Applicant: ViOptix, Inc., Newark, CA (US)

(72) Inventors: Stephen Matthew Kmak, Santa Clara, CA (US); Robert James Mosley, San Jose, CA (US); David Keith Hohl, Milpitas, CA (US); Willem-Jan Ouburg, San Leandro, CA (US); Timothy Lee Sauder, Mountain View, CA (US); Alan Baldwin, San Jose, CA (US)

(73) Assignee: ViOptix, Inc., Newark, CA (US)

( * ) Notice: Subject to any disclaimer, the term of this patent is extended or adjusted under 35 U.S.C. 154(b) by 1039 days.

(21) Appl. No.: 17/146,186

(22) Filed: Jan. 11, 2021

(65) Prior Publication Data

US 2021/0212614 A1    Jul. 15, 2021

Related U.S. Application Data

(60) Provisional application No. 62/959,778, filed on Jan. 10, 2020.

(51) Int. Cl.
*A61B 5/1455* (2006.01)

(52) U.S. Cl.
CPC .... *A61B 5/14552* (2013.01); *A61B 2562/166* (2013.01); *A61B 2562/227* (2013.01)

(58) Field of Classification Search
CPC .......... A61B 5/14552; A61B 2562/166; A61B 2562/227
See application file for complete search history.

(56) References Cited

U.S. PATENT DOCUMENTS

| 5,517,301 A | 5/1996 | Dave |
| 5,991,652 A | 11/1999 | Barthelemy et al. |

(Continued)

FOREIGN PATENT DOCUMENTS

| CN | 202950646 U | 5/2013 |
| CN | 204863117 U | 12/2015 |

(Continued)

OTHER PUBLICATIONS

Extended European Search Report for European Patent Application No. 21738212.6 dated Apr. 11, 2024, 16 pages.

(Continued)

*Primary Examiner* — Eric F Winakur
(74) *Attorney, Agent, or Firm* — Aka Chan LLP

(57) ABSTRACT

An oximetry device includes an inductive detector. When the oximetry device is sealed in a sheath and a latch of the sheath is in a latched position, the inductive detector inductively detects that latch. The oximeter device uses first information received from the detector for the latch being in the latched position to allow the device to take oximetry measurements. The oximeter device uses second information received from the detector for the latch not being in the latched position to allow the device to display a message on a display of the device that the sheath is not sealed. The displayed message indicates to a user that the sheath lid needs to be closed. The closed lid prevents contaminants in the sheath from reaching patient tissue during use of the device and sheath.

29 Claims, 23 Drawing Sheets

(56) References Cited

U.S. PATENT DOCUMENTS

| | | | |
|---|---|---|---|
| 6,516,209 B2 | 2/2003 | Cheng et al. | |
| 8,233,955 B2 | 7/2012 | Al-Ali et al. | |
| 8,750,954 B2 | 6/2014 | Petersen et al. | |
| 8,798,700 B1 | 8/2014 | Heaton, II et al. | |
| 9,398,870 B2 | 7/2016 | Bechtel et al. | |
| 10,722,156 B2 | 7/2020 | Lonsinger et al. | |
| 2002/0170823 A1 | 11/2002 | Housefield et al. | |
| 2006/0039139 A1 | 2/2006 | Maglica et al. | |
| 2008/0015424 A1 | 1/2008 | Bernreuter | |
| 2008/0319290 A1 | 12/2008 | Mao et al. | |
| 2009/0018405 A1 | 1/2009 | Katsumura et al. | |
| 2011/0205535 A1 | 8/2011 | Soller et al. | |
| 2013/0023772 A1 | 1/2013 | Kinsley et al. | |
| 2013/0317373 A1 | 11/2013 | Warren et al. | |
| 2015/0190079 A1 | 7/2015 | Yamaji et al. | |
| 2017/0049336 A1 | 2/2017 | Hatch | |
| 2017/0112391 A1 | 4/2017 | Stivoric et al. | |
| 2017/0287963 A1* | 10/2017 | Rudmann | H01L 27/14621 |
| 2017/0303836 A1 | 10/2017 | Bechtel et al. | |
| 2018/0340833 A1 | 11/2018 | Liang | |
| 2020/0111768 A1* | 4/2020 | Last | H01L 27/14618 |

FOREIGN PATENT DOCUMENTS

| | | |
|---|---|---|
| JP | 4846181 | 12/2011 |
| JP | 2019201978 A | 11/2019 |
| KR | 10-2011-0053993 | 5/2011 |
| WO | 200212854 A2 | 2/2002 |
| WO | WO2011008382 | 1/2011 |
| WO | WO2011127063 | 10/2011 |
| WO | WO2012100090 | 7/2012 |

OTHER PUBLICATIONS

International Search Report, PCT Application PCT/US2021/012999, Jun. 15, 2021, 4 pages.

* cited by examiner

MEDICAL DEVICE AND SHEATH SEAL AND SEAL VERIFICATION

CROSS-REFERENCE TO RELATED APPLICATIONS

This application claims the benefit of U.S. patent application 62/959,778, filed Jan. 10, 2020. This application is incorporated by reference along with all other references cited in these applications.

BACKGROUND OF THE INVENTION

The present invention relates generally to optical systems that monitor parameters related to oxygen levels in tissue. More specifically, the present invention relates to optical probes, such as compact, handheld oximeters, and sheaths for the optical probes that shield the optical probes from contaminants during use and communicate status information to the optical probes regarding contaminant protection so that the optical probes are reusable.

Oximeters are medical devices used to measure the oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated hemoglobin, deoxygenated hemoglobin, melanin, water, lipid, and cytochrome. Oxygenated and deoxygenated hemoglobins are generally the dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving the reuse of oximeters; reducing or eliminating contamination during use; improving remote communication; improving measurement accuracy; reducing measurement time; lowering cost through reuse; reducing size, weight, or form factor; reducing power consumption; and for other reasons, and any combination of these.

Therefore, there is a need for improved tissue oximetry devices and methods of shielding oximetry devices during use for reuse of the devices.

BRIEF SUMMARY OF THE INVENTION

Embodiments relate to compact, handheld oximeters and sheaths that house and shield the handheld oximeters from patient contact and contaminants during use and shield patients from contaminants on the handheld oximeters. Because a handheld oximeter is located in a sheath and cannot contaminate patient tissue, the handheld oximeter can be reused.

In an implementation, a device includes a top housing comprising a display visible from an exterior of the top housing. A bottom housing of the device includes a printed circuit board, a processor formed on the printed circuit board, a probe tip coupled to the processor, and a first wall. The first wall includes a front side surface, a backside surface, and an opening extending from the front side surface to the backside surface. The printed circuit board is coupled to the front side surface of the first wall. The printed circuit board includes a plurality of electrical contacts located on the back surface and coupled to the processor. The electrical contacts on the backside surface of the printed circuit board are visible through the opening formed in the first wall of the bottom housing. The backside surface of the first wall comprises a first riser that extends from the backside surface of the first wall, the first riser comprises a sidewall, an angle between at least a portion of the sidewall of the first riser and the backside surface of the first wall the is less than a straight angle.

A detachable battery that couples to the device couples to the sidewall of the riser. Because the angle of the sidewall of the riser is less than a straight angle, a force applied to a top of the battery in the direction of the sidewall can transfer the force to the device. The force when applied to the top of the battery in a sheath can force the device into the sheath and can force a probe face of the device into contact with a sensor window of the sheath. Thus, the probe face and sensor window will remain in contact while the device and sheath are used, even if the device and sheath are inverted.

In an implementation, a sheath includes a top and a body where the top opens to provide an opening where a handheld oximeter can be placed into the body of the sheath. The top of the sheath can be closed onto the body and the closure of the top can be verified by circuits in the handheld oximeter. The circuits can monitor the position of a latch that is connected to the top of the sheath. The circuits can determine when the latch is unlatched and the top is open and not sealed closed to the body. And, the circuits can determine when the latch is latched and the top is closed and sealed to the body.

In an implementation, a sheath communicates sheath status information to a handheld oximeter to verify that the sheath is a validated sheath that is permitted to operate in combination with the handheld oximeter. A validated sheath having a known and trusted configuration facilitates the reuse of a handheld oximeter because the oximeter is known to remain free of contaminants during the use of the oximeter. The communication between the sheath and handheld oximeter can be wireless using near-field communication (NFC) devices and NFC communication protocols or other circuit types and other communication protocols.

The sheath can include windows that allow light from a handheld oximeter to pass through the windows during the use of the oximeter. A first window can be proximate to a display of the handheld oximeter so that the display can be viewed by a user during use. A second window can be proximate to a probe face of a handheld oximeter so that the oximeter can emit light into tissue and collect the light after reflection from the tissue so that oximetry measurements can be made for the tissue. The windows are sealed to the sheath and keep the handheld oximeter from becoming contaminated during use.

The handheld oximeters implementations are entirely self-contained, without any need to connect, via wires or wirelessly, to a separate system unit for making oximetry measurements. The sources and detectors of the oximetry device are arranged in an arrangement having various source-detector pair distances that allow for robust calibration, self-correction, and spatially-resolved spectroscopy in a compact probe. Other source-detector arrangements are also possible.

In an implementation, the handheld oximeter is a tissue oximeter that can measure oxygen saturation without requiring a pulse or heartbeat. A tissue oximeter of the invention is applicable to many areas of medicine and surgery, including plastic surgery. The tissue oximeter can make oxygen saturation measurements of tissue where there is no pulse; such tissue, for example, may have been separated from the body (e.g., a flap) and will be transplanted to another place in the body. The tissue oximeter can also make oxygen saturation measurements of tissue where there is a weak pulse, such as where perfusion is relatively low.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
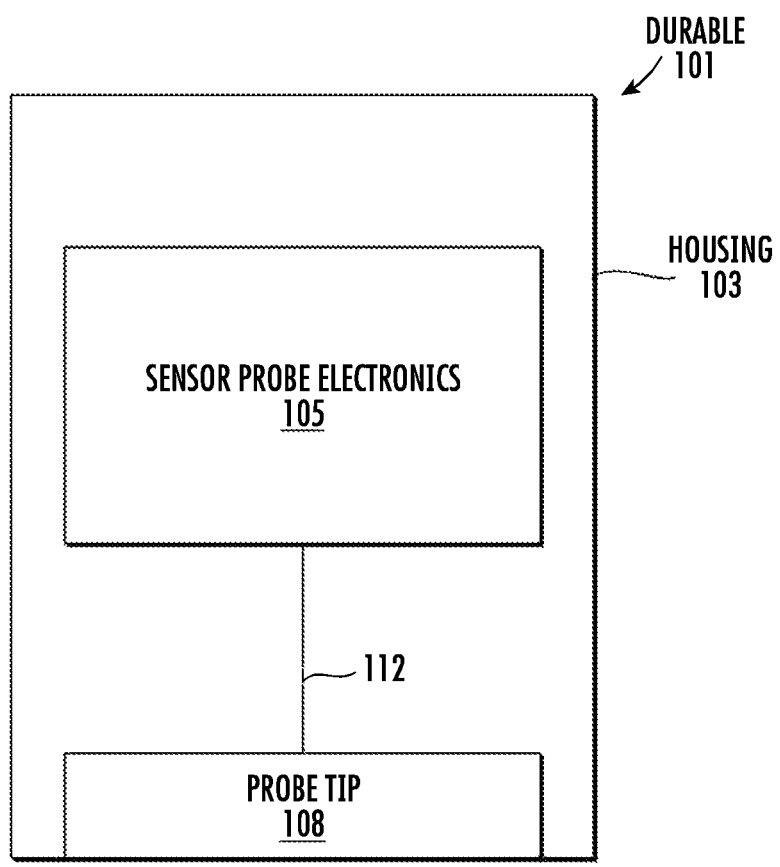
FIG. 1 shows a block diagram of a system unit for measuring various oximetry parameters of patient tissue.

Spectroscopy has been used for noninvasive measurements of various physiological properties in animal and human subjects. Visible (e.g., red light, green light, or both) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy has been applied to exploit these different absorption features for measuring oxygen levels in physiological media, such as tissue hemoglobin oxygen saturation (sometimes referred to as oxygen saturation) and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficients and the reduced scattering coefficients of the physiological medium by use of the photon diffusion approximation, Monte Carlo models, or other techniques. From the absorption coefficients at multiple wavelengths, concentrations of oxygenated and deoxygenated hemoglobins can be determined and from these concentrations, the tissue oxygen saturation can be calculated.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

Alternatively, an SRS instrument may emit light from two or more light sources positioned at different distances from one or more detectors. Scattering of light back to the detectors is caused by relative changes of the index of refraction of the tissue and includes Mie scattering from larger structures such as mitochondria (the majority of tissue scattering is a result of mitochondria) and Rayleigh scattering from smaller structures such as intracellular vesicles. Absorption of light is caused by interaction with the tissue's chromophores.

From the reflectance (i.e., the recovered light intensity), which is recovered as a function of distance (e.g., multiple discrete distances of light detectors) from the light source, an SRS instrument can quantify the absorption coefficient and the scattering coefficient of the tissue at a single wavelength.

Multiple wavelengths of light can then be used with SRS to determine oxygenated and deoxygenated hemoglobin concentrations, and therefore, oxygen saturation within the volume of the tissue probed. Further, the wavelengths of the light source or light sources and the relative positions of the light source(s) with respect to a single detector or multiple ones of the detectors, allow tissue oximetry measurements to be made for a predetermined tissue depth. In an embodiment, one or more of the light sources and one or more of the detector source may emit and detect light so that oximetry measurements may be made for one or more predetermined tissue depths.

One field in which visible and near-infrared spectroscopy, such as SRS, is useful is in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of non-ideal conditions.

Oximetry probes adapted for SRS and other spectroscopies can come into contact with tissue, other surfaces, fluids (both liquid and gas), or other elements that can contaminate the probes. An oximetry probe that contacts tissue, for example, can be contaminated by the tissue, bacteria on the tissue, viruses on the tissue, tissue fluid, debris on the tissue, the environment near the tissue, any one of these substances, other substances, or any combination of these substances. A sheath can shield an oximetry probe from contaminants, but the efficacy of a sheath can be compromised in a number of ways. The ways in which a sheath can be compromised, allowing an oximetry probe to be contaminated, can be known and unknown. For example, a sheath housing an oximetry device may open and allow contaminants to contact the oximetry probe. The sheath opening may be relatively small and not detectable by visual inspection and the small opening may allow contaminants to enter the sheath and contact the oximetry probe. The efficacy of a sheath can be compromised if the sheath has been previously used and the previous use is unknown. The efficacy of a sheath can also be compromised if the sheath is provided from an unknown source and the sterility or sanitation of the sheath is unknown. Either inside or outside surfaces of the sheath, or both, can be contaminated if the sheath is provided by an unknown source. If the previous use of a sheath is unknown and the sheath is reused, contaminants on the sheath from an initial use can be spread during subsequent use of the sheath. Sheaths and the oximetry probes in the sheath may be contaminated in a variety of other ways. Reuse of an oximetry probe after contamination may be precluded or may increase the cost of reuse due to the cost of sanitizing or sterilizing the oximetry probe. Oximetry probes and sheaths of the present invention are directed toward improved sanitation, sterilization, or both.

FIG. 1 shows a system unit 101 for measuring various parameters of tissue in a patient. System unit 101 is sometimes referred to as a durable system unit because the unit is reusable, such as when the unit is used in combination with a protective sheath. The parameters of the tissue measured by the system unit may include an oxygen saturation level (relative oxygen saturation, absolute oxygen saturation, or both), a total hemoglobin concentration, an oxygenated hemoglobin concentration, an deoxygenated hemoglobin concentration, blood flow, pulse rate, a signal level of light reflected from the tissue, melanin concentration of tissue, homogeneity of a tissue quality, other tissue parameters, or any combination of the parameters. The system unit includes housing 103, sensor probe electronics 105, and a probe tip 108, which is connected to the sensor probe electronics via a wired connection 112. Connection 112 may be an electrical connection, an optical connection, or another wired connection including any number of wires (e.g., one, two, three, four, five, six, or more wires or optical fibers), or any combination of these or other types of connections. In other implementations, connection 112 may be a wireless connection, such as via a radio frequency (RF) or infrared (IR) connection.

Typically, the system unit is used by placing the probe tip in contact or close proximity to tissue (e.g., skin or internal organ or other tissue) at a site where tissue parameter measurements are desired. The system unit causes an input signal to be emitted by the probe tip into the tissue (e.g., human tissue). There may be multiple input signals, and these signals may have varying or different wavelengths of electromagnetic radiation. The input signal is transmitted into the tissue and reflected from the tissue, absorbed by the tissue, or transmitted through the tissue.

Then, after transmission through the tissue or reflection from the tissue, the signal is received at the probe tip. This received signal is received and analyzed by the sensor probe electronics. Based on the received signal, the sensor probe electronics determine various parameters of the tissue, such as an oxygen saturation level, a total hemoglobin concentration, an oxygenated hemoglobin concentration, an deoxygenated hemoglobin concentration, a blood flow, a pulse, a signal level of light reflected from the tissue, melanin concentration of tissue, or other tissue parameters. One or any combination of these parameters can be displayed on a display screen of the system unit.

In an implementation, the system unit is a tissue oximeter, which can measure oxygen saturation and hemoglobin concentration, without requiring a pulse or heartbeat. A tissue oximeter of the invention is applicable to many areas of medicine, surgery (including plastic surgery and spinal surgery), post-surgery, athlete monitoring, and other uses. The tissue oximeter can make oxygen saturation and hemoglobin concentration measurements of tissue where there is no pulse, such as tissue that has been separated from the body (e.g., a tissue flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. There are various implementations of systems and techniques for measuring oxygen saturation, such as discussed in U.S. patent application Ser. No. 62/959,757, 62/959,764, 62/959,787, 62/959,795, 62/959,808, filed Jan. 10, 2020; U.S. Ser. Nos. 17/146,176, 17/146,182, 17/146,190, 17/146,194, 17/146,197, 17/146,201, filed Jan. 11, 2021; and U.S. Ser. No. 29/720,112, 29/720,115, 29/720,120, 29/720,122, filed Jan. 9, 2020. These patent applications are incorporated by reference along with all other references cited in these applications.

Figure 2:
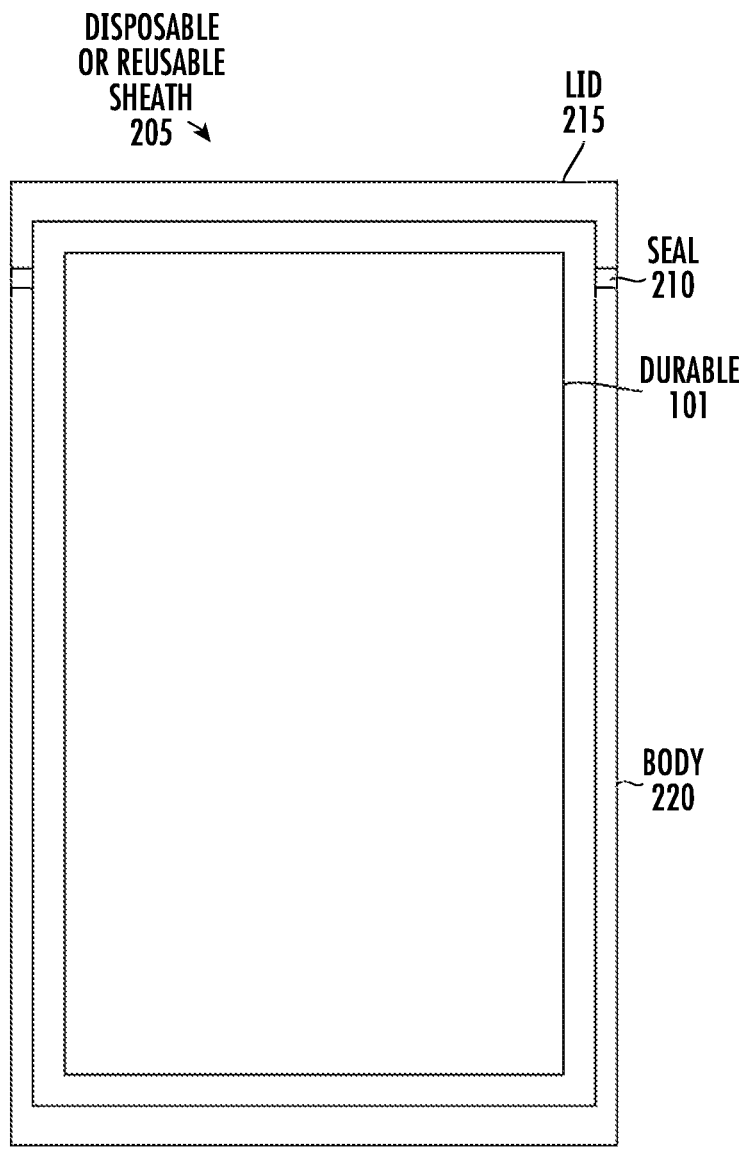
FIG. 2 shows a block diagram of the system unit housed in a sheath.

FIG. 2 shows system unit 101 housed in a sheath 205. The sheath includes a lid 215 and a body 220, which may be sealed to the lid via a seal 210. The lib may be separable from the body or may be connected to the body, such as via a hinge. The hinge may allow the lid to rotate to seal the lid to the body. The sheath may be a disposable sheath or a sheath that is reusable. For example, the system unit and sheath may travel with a patient from surgery (e.g., use) to post-surgery (e.g., reuse) for tissue monitoring.

With the lid opened, the system unit may be inserted into the sheath, and thereafter the lid may be sealed to the body to house and seal the system unit in the sheath. The system unit may then be used to make tissue parameter measurements in the sealed environment provided by the sheath. The sheath can protect the system unit from contacting elements that the sheath contacts, such as tissue, tissue fluid, biological agents (e.g., bacteria, viruses, prions, and pyrogens), debris, and other contaminants. When the lid is open and the seal is broken, the system unit may be removed from the sheath. Because the system unit is sealed into the sheath by the body, lid, and seal, the system unit can remain relatively clean, sanitized, or sterile for reuse.

The sheath can also protect the tissue of a patient from contacting elements that are on a system unit that is inside the sheath. The sheath can prevent patient tissue from contacting bacteria, viruses, prions, pyrogens, other contaminants, or any one of these contaminants that might be on the system unit from passing through the sheath seal and contacting patient tissue.

Figure 3:
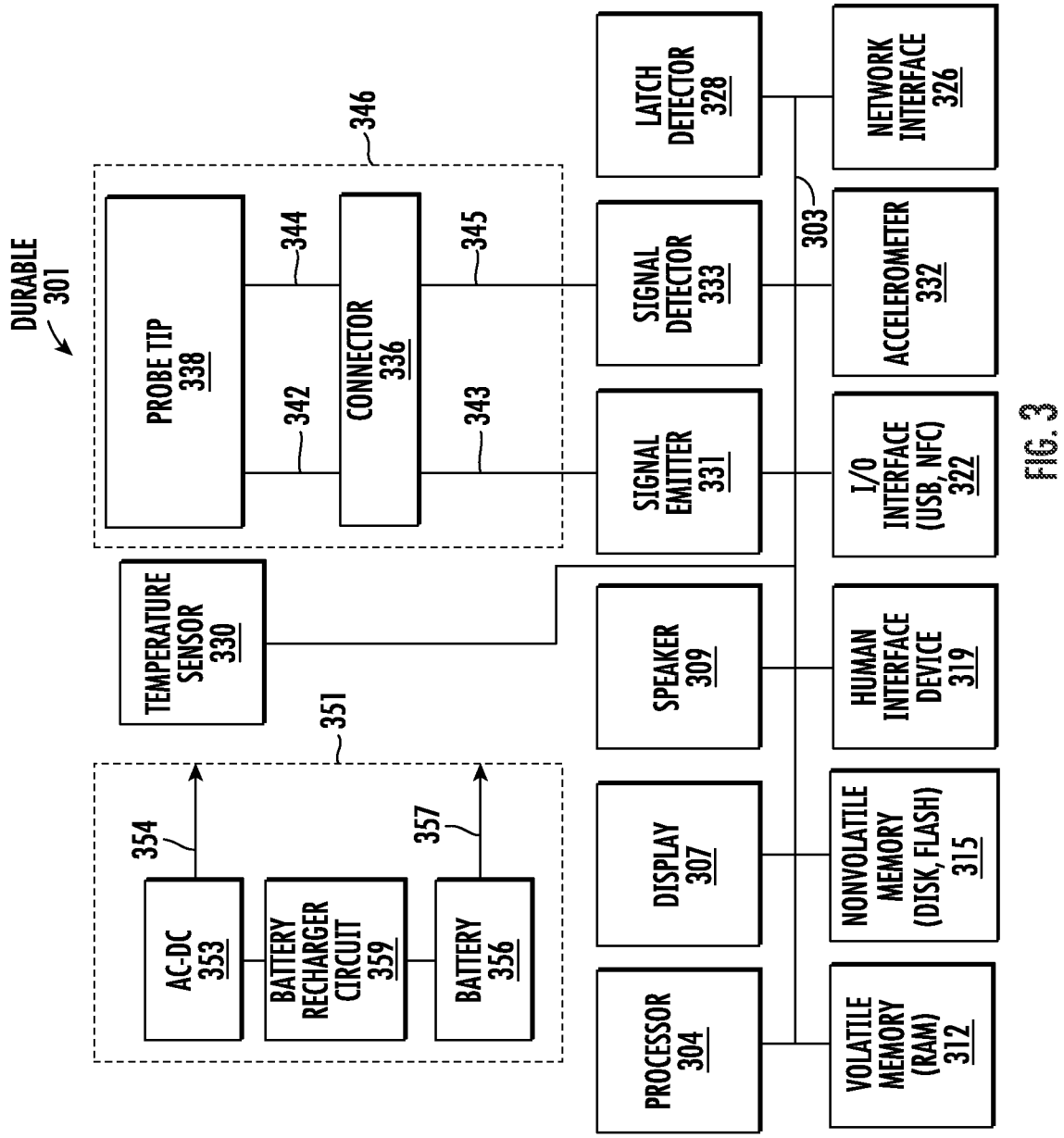
FIG. 3 shows a block diagram of the system unit, in an implementation.

FIG. 3 shows a block diagram of system unit 301, in an implementation. The system unit includes a processor 304, display 307, speaker 309, signal emitter 331, signal detector 333, volatile memory 312, nonvolatile memory 315, human interface device (HID) 319, input-output (I/O) interface 322, network interface 326, latch detector 328, temperature sensor 330, and accelerometer 332. These components are housed within housing 103. Different implementations of the system may include any number of the components described, in any combination or configuration, and may also include other components not shown.

The components are linked together via a bus 303, which represents the system bus architecture of the system unit. Although FIG. 3 shows one bus that connects to each component of the system unit, bus 303 is illustrative of any interconnection scheme that links the components of the system unit. For example, one or more bus subsystems can interconnect one or more of the components of the system unit. Additionally, the bus subsystem may interconnect components through one or more ports, such as an audio port (e.g., a 2.5-millimeter or 3.5-millimeter audio jack port), a universal serial bus (USB) port, or other port. Components of the system unit may also be connected to the processor via direct connections, such as direct connections through a printed circuit board (PCB).

In an implementation, system unit 301 includes a sensor probe 346. The sensor probe includes a probe tip 338 and a connector 336. The probe tip is connected to the connector via a first communication link 342 and a second communication link 344. First communication link 342 may include an electrical wire, a set of electrical wires (e.g., a ribbon cable), a waveguide (e.g., fiber optic cables), a set of waveguides (e.g., a set of fiber optic cables), a wireless communication link, or any combination of these types of links. The second communication link may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The electrical wire or sets of electrical wires of the first communication link, the second communication link, or both can include one or more electrical traces on a printed circuit board.

The connector connects (e.g., removably connects) the probe tip, the wires, waveguides, or any combination of these elements to the signal emitter and signal detector of the system unit. For example, a communication link 343 may connect the signal emitter to the connector and a communication link 345 may connect the signal detector to the connector. Each of the communication links 343 and 345 may include an electrical wire, a set of electrical wires (e.g., a ribbon cable) one waveguide, a set of waveguides, a wireless communication link, or any combination of these links. Each communication link can also include one or more electrical traces on a printed circuit board. For example, the connector may include one or more connectors that are mounted on a PCB. Communication links 342, 344, or either one of these links may be ribbon cables that connect to the probe tip and connect to connectors mounted on a PCB. In this implementation, communication links 343 and 345 can be electrical traces on the PCB that link to the single emitter, signal detector, temperature sensor, or any combination of these. In this implementation, the signal emitters and signal detectors may be electrical emitters and detectors that control light emitters, light detectors, or both in the probe tip.

In an implementation, where the probe tip is separable from the system unit 301, connector 336 may have a locking feature, such as an insert connector that may twist or screw to lock. If so, the connector is more securely held to the system unit and it will need to be unlocked before it can be removed. This will help prevent the accidental removal of the probe tip from the system unit.

The connector may also have a first keying feature, so that the connector can only be inserted into a connector receptacle of the system unit in one or more specific orientations. This will ensure that proper connections are made.

The connector may also have a second keying feature that provides an indication to the system unit a type of probe (e.g., a probe from many different types of probes) that is attached. The system unit may be adapted to make measurements for a number of different types of probes. When a probe is inserted in the system unit, the system uses the second keying feature to determine the type of probe that is connected to the system unit. Then the system unit can perform the appropriate functions, use the appropriate algorithms, or otherwise make adjustments in its operation for the specific probe type.

In an implementation, signal emitter 331 includes one or more light sources that emit light at one or more specific wavelengths. In a specific implementation, the light sources emit five or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs).

In an implementation, signal emitter 331 is an emitter that emits electrical signals to one or more light sources, which may emit light based on the received electrical signals. In some implementations, the signal emitter includes one or more light sources and electrical signal emitters that are connected to the light sources.

In an implementation, signal detector 333 includes one or more photodetectors capable of detecting the light at the wavelengths produced and emitted by the signal emitter. In another implementation, the signal detector 333 is an electrical signal detector that detects electrical signals generated by one or more photodetectors. In another implementation, the signal detector includes one or more photodetectors and one or more electrical detectors that are connected to the photodetectors.

In an implementation, HID 319 is a device that is adapted to allow a user to input commands into the system unit. The HID may include one or more buttons, one or more slider devices, one or more accelerometers, a computer mouse, a keyboard, a touch interface device (e.g., a touch interface of display 307), a voice interface device, or another HID.

In an implementation where the HID is an accelerometer and the system unit is a handheld unit, the accelerometer may detect movements (e.g., gestures) of the system unit where the system unit may be moved by a user. Movements may include a left movement, right movement, forward movement, back movement, up movement, down movement, one or more rotational movements (e.g., about one or more axes of rotation, such as the x-axis, y-axis, z-axis, or another axis), any combinations of these movements, or other movements.

Information for the various movements detected by the accelerometer may be transmitted to the processor to control one or more systems of the system unit. For example, an upward movement (e.g., a lifting movement) may be transmitted to the processor for powering on the system unit. Alternatively, if the system unit is set down and left unmoved for a predetermined period of time, then the processor may interpret the lack of movement detected by the accelerometer as a standby mode signal and may place the system unit in a standby power mode (a lower power mode than a normal operation mode where oximetry measurements can be made by the system unit), or a power-down signal and may power down the system unit.

When the system unit is powered on, information for a left movement or a right movement detected by the accelerometer and transmitted to the processor may be used by the processor to control the system unit. For example, a left or right movement of the system unit may be used by the processor to change menu items displayed on the display. For example, the processor may use the information for a left movement to scroll menu items on the display to the left (e.g., scroll a first menu item left and off of the display to display a second menu item on the display). The processor may use the information for a right movement of the system unit to scroll menu items to the right (e.g., scroll a first menu item right and off of the display, and display a second menu item on the display).

The HID and processor may be adapted to detect and use various movements to activate a menu item that is displayed on the display. For example, information for an upward movement or a downward movement may be detected and used to activate a menu item that is displayed on the display. For example, if a user is prepared to take an oximeter measurement and a menu option is displayed for taking an oximeter measurement, a quick downward movement of the system unit may start a measurement when the probe tip is placed in contact with tissue The HID may include one or more accelerometers to detect motion in various directions (e.g., linear, rotational, or both). The accelerometers can include one or more capacitive micro-electro-mechanical system (MEMS) devices, one or more piezoresistive devices, one or more piezoelectric devices, or any combination of these devices.

In an embodiment, accelerometer 332 is adapted to detect relatively high G-force accelerations associated with a shock that the system unit experiences. The shock may be from bumping the system into something, dropping the system unit (e.g., dropping the system unit on a table or the floor), or other shock events. In an implementation, if the accelerometer indicates to the processor that a shock event has occurred, the processor can take a number of actions. For example, the processor can shut down the system unit. The processor can display one or more messages on the display. The messages may indicate that the system unit should be recalibrated. The message may indicate that contact between the system unit and the sheath should be checked. The accelerometer may include one or more capacitive micro-electro-mechanical system (MEMS) devices, one or more piezoresistive devices, one or more piezoelectric devices, or any combination of these devices.

In an implementation, the latch detector 328 is adapted to detect whether a latch of the sheath is latched or unlatched. If the latch is latched, then the system unit is housed and enclosed in the sheath. In this configuration, with the system unit housed and enclosed in the sheath, the system unit may not be contaminated by material contacting the outside surface of the sheath. If the latch is unlatched and the system unit is in the sheath, then the system unit might be contaminated with material contacting the outside surface of the sheath. That is, the seal that seals the lid of the sheath to the body of the sheath may be unsealed (i.e., opened) and contaminates may pass from outside of the sheath to the inside of the sheath where the system unit is located.

In an implementation, at least a first portion of the latch is metal. Other portions of the latch may be metal or other material, such as a plastic material. The first portion of the latch is a first distance from the latch detector when the latch is latched and is a second distance from the latch detector when the latch is unlatched. The first distance is less than the second distance.

In an implementation, the latch detector includes an inductor that can inductively couple to the first portion of the latch. The inductor can be driven with a direct current or an alternating current and thus detect when the first portion of the latch moves toward the latch detector or away from the latch detector. The latch detector can be calibrated so that the latch detector can detect when the latch moves to the first distance away from the latch detector or farther than the first distance away from the latch detector. The latch detector can include an analog-to-digital converter, a digital signal processor (DSP), or both that digitize and analyze the current flowing through the inductor. One or both of these circuits can communicate the digitalized information to the processor that can determine whether the latch is open or closed. The processor can display a message on the display to indicate whether the latch is open or closed, whether the seal for the sheath is sealed or unsealed, warn of potential contamination, or other messages associated with the latch being opened or closed.

In an embodiment, the latch detector is a capacitive detector that can capacitively couple to the latch. The capacitive detector can detect the latch in the latched position at a first distance from the capacitive detector and moving away from the latched position and the first distance.

The nonvolatile memory 315 may include a FLASH memory, other nonvolatile solid-state storage (e.g., USB flash drive), battery-backed-up volatile memory, tape storage, reader, and other similar media, and combinations of these. In some implementations, the nonvolatile memory includes a mass disk drive, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc). The volatile memory may include a random access memory (RAM).

The processor may include a microcontroller, a microprocessor, an application specific integrated circuit (ASIC), programmable logic (e.g., field programmable gate array), or any combination of these circuits. The processor may include multiple processors or a multicore processor, which may permit parallel processing of information.

In an implementation, the system unit is part of a distributed system. In a distributed system, individual systems are connected to a network and are available to lend resources to another system in the network as needed. For example, a single system unit may be used to collect results from numerous sensor probes at different locations.

Aspects of the invention may include software executable code, firmware (e.g., code stored in a read only memory (ROM) chip), or both. The software executable code or firmware may embody algorithms used in making oxygen saturation measurements of the tissue. The software executable code or firmware may include code to implement a user interface by which a user uses the system, displays results on the display, selects or specifies parameters that affect the operation of the system, or execute algorithms and calculations to generate a result.

Further, a computer-implemented or computer-executable version of the invention may be embodied using, stored on, or associated with a computer-readable medium. A computer-readable medium may include any medium that participates in providing instructions to one or more processors for execution. Such a medium may take many forms, including but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, MATLAB (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows XP, Windows XP x64 Edition, Windows Vista, Windows CE, Windows 7, Windows 8, Windows 10, Windows Mobile), Linux, HP-UX, UNIX, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may communicate with other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11 g, 802.11i, and 802.11n, just to name a few examples). For example, signals from a system may be transferred, at least in part, wirelessly to components or other systems or computers.

In an embodiment, through a Web browser or other interface executing on a computer workstation system or another device (e.g., a laptop computer, smartphone, or personal digital assistant), a user accesses the system unit of the invention through a network such as the Internet. The user will be able to see the data being gathered by the system unit. Access may be through the World Wide Web (WWW). The Web browser is used to download Web pages or other content in various formats, including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
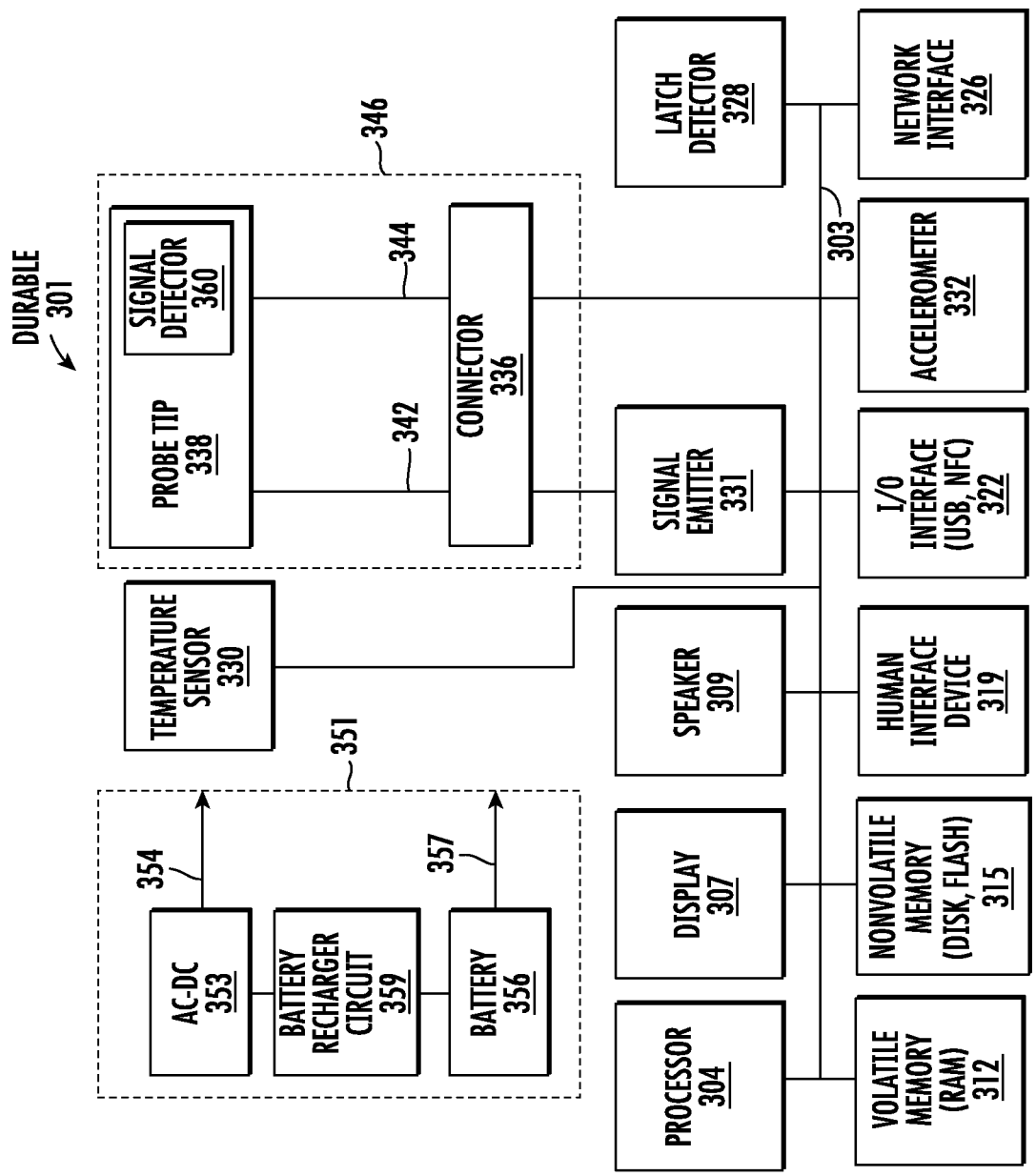
FIG. 4 shows a block diagram of the system unit, in an implementation.

FIG. 4 shows a block diagram of system unit 401, in an implementation. System unit 401 is similar to system unit 301 but differs in that the signal detector 344 is located in probe tip 346. A wire or set of wires (e.g., a ribbon cable) may connect the signal detector to the bus and processor. For example, a ribbon cable that is connected to the signal detector may also be connected to a connector or socket mounted on a PCB that the processor and other circuits are mounted on. The signal detector may be located at a probe face of the probe tip. The signal emitter may be optically located behind the probe face of the probe tip.

Figure 5:
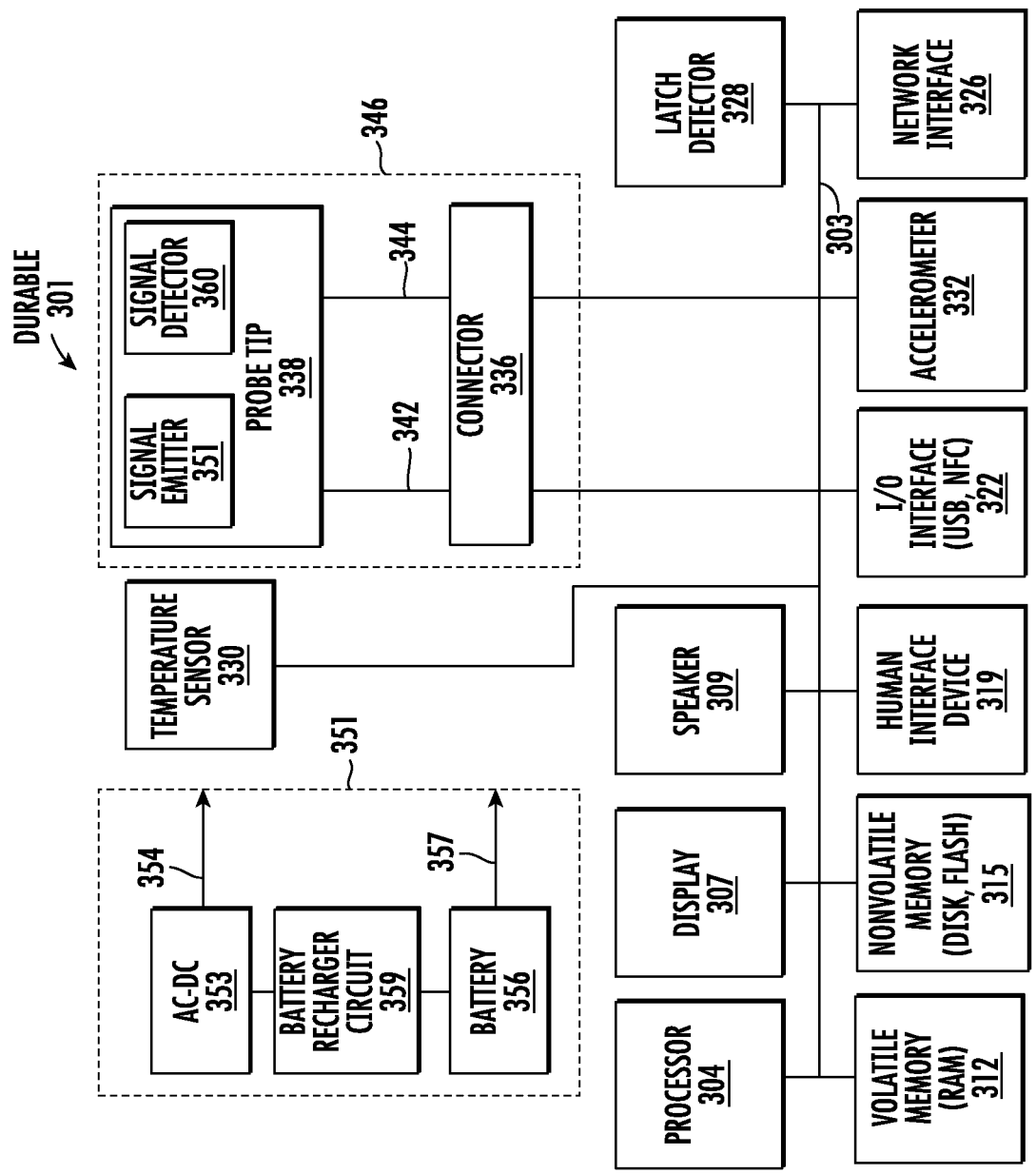
FIG. 5 shows a block diagram of the system unit, in an implementation.

FIG. 5 shows a block diagram of system unit 501, in an implementation. System unit 501 is similar to system units 301 and 401 but differs in that the signal emitter 331 and the signal detector 344 are located in probe tip 346. A wire or wires (e.g., one or more ribbon cables) may connect the signal emitter, the signal detector, or both to the bus and processor. A first ribbon cable may connect the signal emitter to the bus and processor and a second ribbon cable may connect the signal detector to the bus and processor. For example, the first ribbon cable that is connected to the signal emitter may also be connected to a connector or socket mounted on a PCB that the processor and other circuits are mounted on, and the second ribbon cable that is connected to the signal detector may also be connected to a connector or socket mounted on the PCB. The signal detector may be located at a probe face of the probe tip. The signal emitter may be optically located behind the probe face of the probe tip.

In an implementation, connector 336 includes a locking feature, such as an insert connector that inserts into a connecting port and then twists or screws to lock. If so, the connector is more securely held to the system unit and it will need to be unlocked before it can be removed. This will help prevent accidental removal of the probe.

In an implementation, connector 336 includes one or more PCBs that are connected to one or more wires (e.g., ribbon cables) that connect to the signal emitter, the signal detector, or both. For example, a first ribbon cable may connect to a first PCB that connects to the signal emitter. A second ribbon cable may connect to a second PCB that connects to the signal detector.

Block 351 shows a power block of the system unit having both AC and battery power options. In an implementation, the system includes an AC-to-DC converter 353, such as a full-wave rectifier. The converter takes AC power from a wall socket, converts AC power to DC power, and the DC output is connected (indicated by an arrow 354) to the components of the system unit needing power.

In an implementation, the system is battery operated. The DC output of a battery 356 is connected (indicated by an arrow 357) to the components of the system unit needing power. The battery may be recharged via a recharger circuit 359, which received DC power from the AC-to-DC converter. The AC-to-DC converter and recharger circuit may be combined into a single circuit. In an implementation, the battery is rechargeable via magnetic charging or induction charging.

In an implementation, block 351 is a battery module that includes one or more batteries that power the components of the system unit. The batteries may be rechargeable or disposable batteries. The block may not include the AC-to-DC converter. Block 351 may be a block that is integrated with the system unit or is separable from the system unit.

Figure 6:
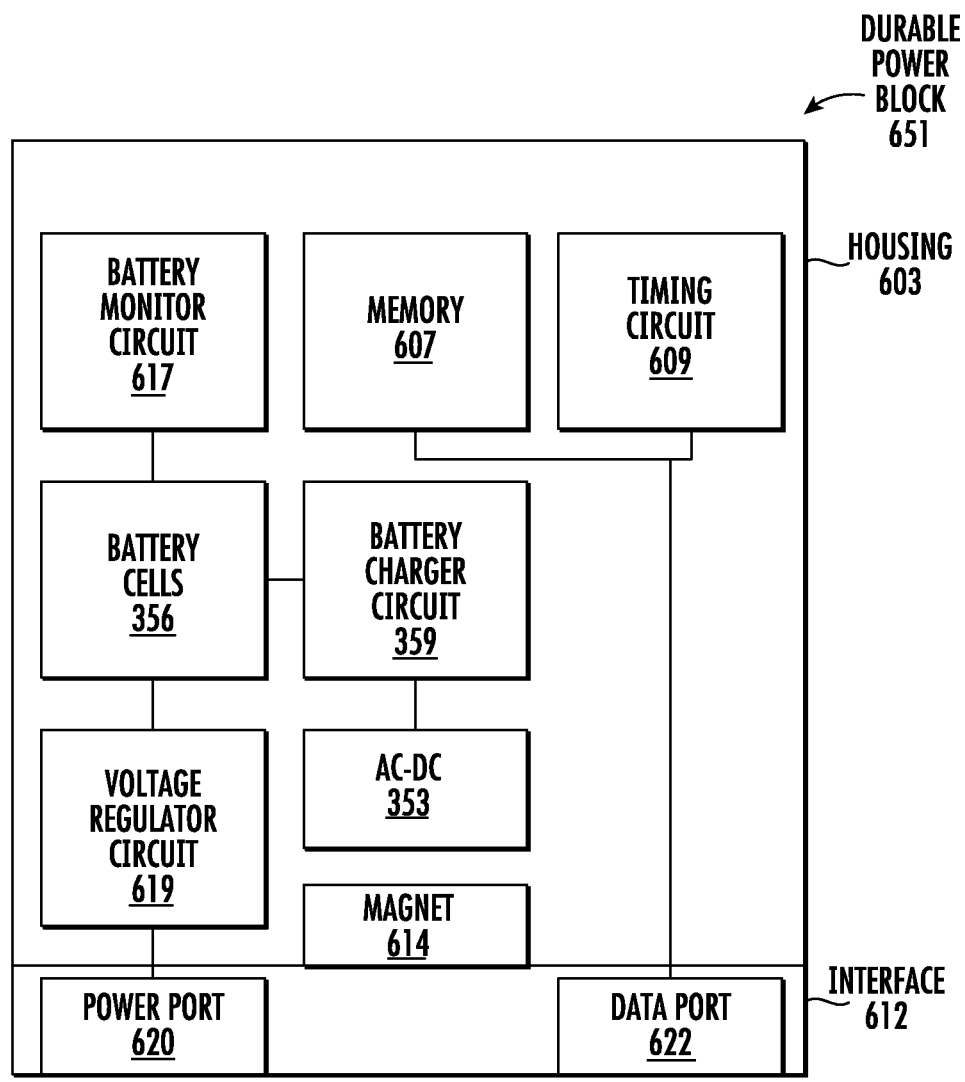
FIG. 6 shows a diagram of the power block of the system unit, in an implementation.

FIG. 6 shows block 651 that is a power block, in an implementation. Block 651 is similar to block 351 but may include a battery monitor 617, a voltage regulator circuit 619, a memory 607, a timing circuit 609, an interface 612, which includes a power port 620 and a data port 622, a magnet 614, other circuits, or any combination of these circuits.

Battery monitor 617 may be connected to the battery cells 356 and may monitor the capability of the battery cells. For example, the battery monitor may determine a current charge state, such as a percentage of the total possible charge. The battery monitor may determine the charge capacity of the battery cells. The charge capacity may be a percentage of the charge capacity compared to the charge capacity of the battery cells when new. The battery monitor may determine the maximum power delivery capability of the battery.

The battery cells may be disposable battery cells, such as alkaline battery cells, or rechargeable battery cells, such as nickel-metal hydride, lithium battery cells (e.g., Li/FeS2 size AA, AAA, N, CR123, 18650, or others), lithium polymer, or other types of cells. The power back may include four battery cells that are AA size cells that output 1.5 volts. The four batteries may be in series to output 6 volts, or may be in series and parallel to output 3 volts.

Voltage regulator circuit 619 may be connected between the battery cells and the power port of the battery interface 612. The voltage regulator circuit conditions the voltage output from the battery to output an approximately constant voltage. The voltage regular circuit may also include a DC-to-DC converter that converts a first voltage output from the battery cells to a second voltage that is different from the first voltage.

The timing circuit is a circuit that determines the amount of time length that the battery has been used. Information for the amount of time may be stored in the memory and may be transferred through the data port to the processor when the processor queries the memory for the information. In an implementation, the processor of the system unit can write to the memory of the durable power block to update various information of the power block, such as the power block firmware, the amount of time that the power block has been used, updated identification information for the power block (e.g., an encrypted identifier), or other information.

In an embodiment, the memory may also store an encrypted identifier that identifies the power block. The processor may be adapted to retrieve the encrypted identifier via the power blocks data port. The processor or another decryption circuit of the system unit may decrypt the encrypted identifier and may identify the power block based on the identifier after decryption. The identifier may identify the manufacturer of the power block or may identify other information about the power block, such as the manufacturing date, the battery cell type, battery cell voltage, elapsed usage time, or any combination of these elements. In an implementation, if the identifier is not a known identifier that is known to the system unit, then the processor with not allow the system unit to operate with the power block. That is, the system unit will not operate with a power block manufactured by an unknown manufacturer. Allowing the system unit to operate with known (e.g., authorized) power blocks, the system unit is assured that the power provided by the power block is within the operating specifications of the system unit. Therefore, the circuits, signal emitters, signal detectors, and other elements of the system unit will operate within predetermined parameters and will not operate outside of the predetermined parameters. Also, using a known battery from a known manufacturer provides that the stem unit will operate for a known period of time so that the system unit will not run out of battery power during a medical procedure, such as a surgery. Operating the system unit according to predetermined parameters, facilitates the system unit making accurate and reliable oximetry measurements.

In an implementation, nonvolatile memory 315 stores one or more identifiers for one or more power blocks that may operate with the system unit. The processor may compare the identifier for the power pack that has been decrypted to the one or more identifiers retrieved from the nonvolatile memory to determine whether the power block will be allowed to operate with the system unit. If the power block is not authorized for use with the system unit, the processor may cause a message to be displayed on the display that indicates that the power block is not authorized for use with the system unit. If the power block is authorized to operate with the system unit, then the system unit may operate to make oximetry measurements without displaying information on the display about the authenticity or the inauthenticity of the power block.

In an implementation, the memory of the power block stores an indicator that indicates whether the battery has been previously used. The indicator may be the time information for the amount of time that the power block has operated. A nonzero use time stored in the memory is an indicator that the power block has been previously used. Alternatively, the indicator may be an identifier of a system unit that the power block has been connected to and provided power to. For example, the nonvolatile memory of the system unit may store an identifier of a system unit. The processor of the system unit may transfer the system identifier of the system unit to the power block for storage in the power block's memory.

When the power block is attached to a system unit, the processor of the system unit may query the power block's memory to retrieve any system identifier that may be stored in the power block's memory. In an implementation, if a system identifier retrieved from the power block's memory is different from the system identifier of the system unit that retrieved the system unit from the power block's memory, then the system unit will not operate with the power block. The implementation attempts to ensure that a power block is fully charged and can be used for the duration of a medical procedure (e.g., a surgery) without the power block running out of stored energy. Ensuring that a power block is unused prior to using the power block during a medical procedure provides that the power block will not run out of power during the procedure and minimize risk to a patient. That is, patient risk is lowered if a system unit used during a procedure does not run out of power and can be used for patient monitoring when required.

In an implementation, when the power block is attached to a system unit, the processor of the system unit may query the power block's memory to retrieve the time information for the amount of time that the power block has operated. In an implementation, if the system unit determines that the power block has been previously used based on the time information, then the system unit will not operate with the power block. Similar to the embodiment described immediately above, ensuring that a power block is unused prior to using the power block during a medical procedure provides that the power block will not run out of power during the procedure and minimize risk to a patient.

The power block may include one more magnets 614 that are arranged in an arrangement, such as a square, a rectangular, or another arrangement. A system unit may also have one or more magnets or one or more metal plates (e.g., ferromagnetic plates) that are arranged in an arrangement that is complementary to the arrangement of magnets in the power block. The magnets of the power block may attract the magnets or metal plates of the system unit when the power block is placed in contact with the system unit. The magnetic attraction between the magnets or plates may hold the power block in place when the system unit is being used.

The power block may include one more plates (e.g., ferromagnetic plates) that are arranged in an arrangement, such as square, rectangular, or another arrangement. The system unit may include one or more magnets that are arranged in a complementary arrangement. The magnets of the system unit may magnetically attract the metal plates of the power block when the power block is placed in contact with the system unit. The magnetic attraction between the magnets and plates may hold the power block in place when the system unit is being used.

In an implementation, the power port of the power block includes at least two electrical contacts (e.g., a power contact and a ground contact) and the data port includes at least two electrical contacts (e.g., a data line and a shared ground contact with the power port). The electrical contacts are arranged in an arrangement, such as in a row, in a square, in a rectangle, another arrangement. The system unit includes a power port that includes at least two electrical contacts (e.g., a power contact and a ground contact) and includes a data port that includes at least two electrical contacts (e.g., a data line and a shared ground contact with the power port). The arrangement of the electrical contacts is complementary to the electrical contacts of the power block.

When the power block is placed in contact with the system unit, the magnetic attraction between the magnets or between the magnets and metal plates forces the electrical contacts of the power port in the system unit into contact with the electrical contacts of the power port of the power block. Also, the magnetic attraction forces the electrical contacts of the data port in the system unit into contact with the electrical contacts of the data port of the power block. As such, electrical power can be transferred from the power block to the system unit to power the circuits and other elements of the system unit, and data can be transferred between the power block and the system unit.

Figure 7:
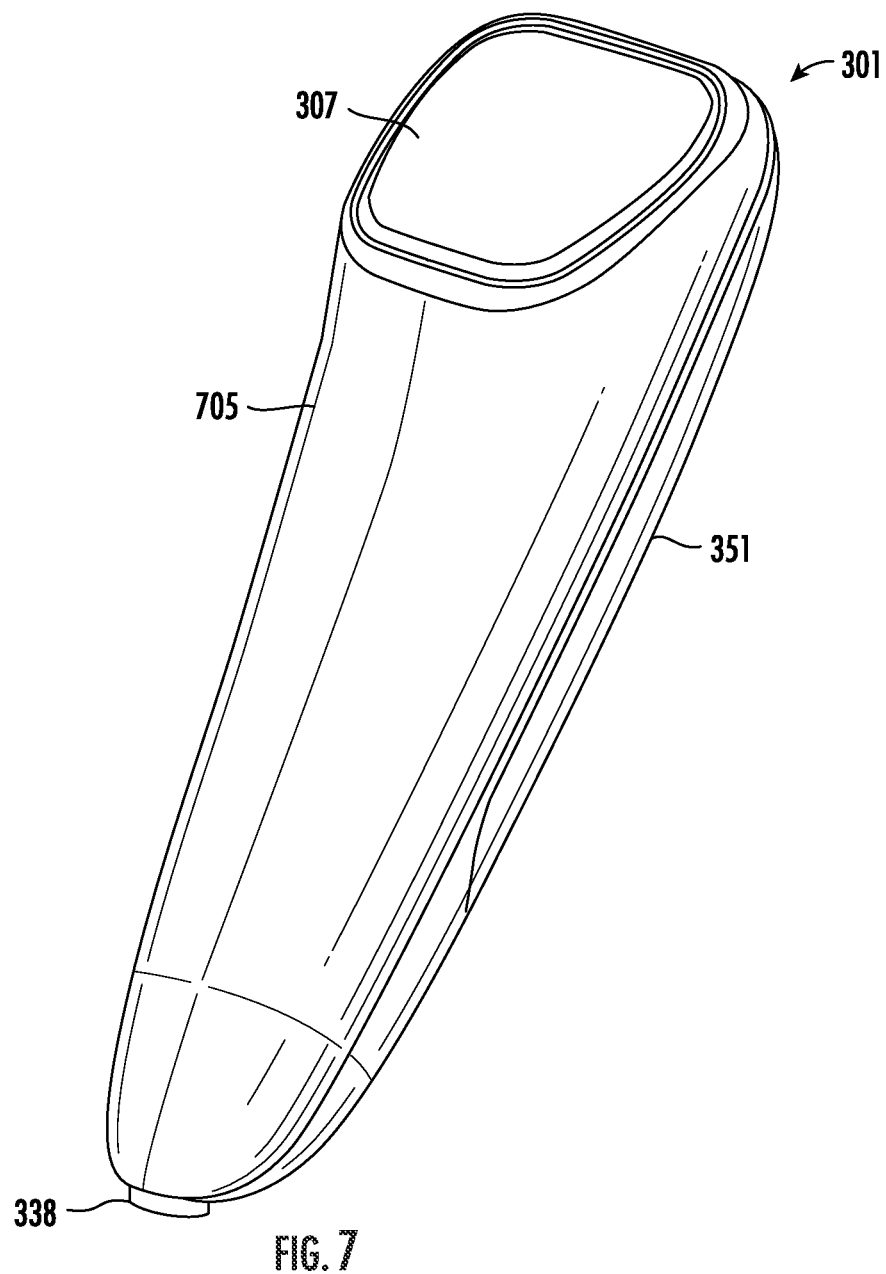
FIG. 7 shows a perspective view of the system unit and power block.

FIG. 7 shows a perspective view of the system unit 301 and power block 351 coupled to the system unit, in an implementation. The display 307 of the system unit is located at a first end of the system unit and the probe tip 338 is located at a second end of the system unit where the first and second ends of proximal and distal ends of the unit. The housing of the system unit tapers from the first end to the second end. The described circuit elements are housed in the housing 705 of the system unit. housing 705 of the system unit. When the second window of the sheath is in contact with tissue, the first window of the sheath and the display of the system unit faces away from the tissue for easy visibility of the display. In an implementation where the system unit is used without a sheath, when the probe face of the system unit is in contact with tissue, the display faces away from the tissue for easy visibility of the display.

Figure 8:
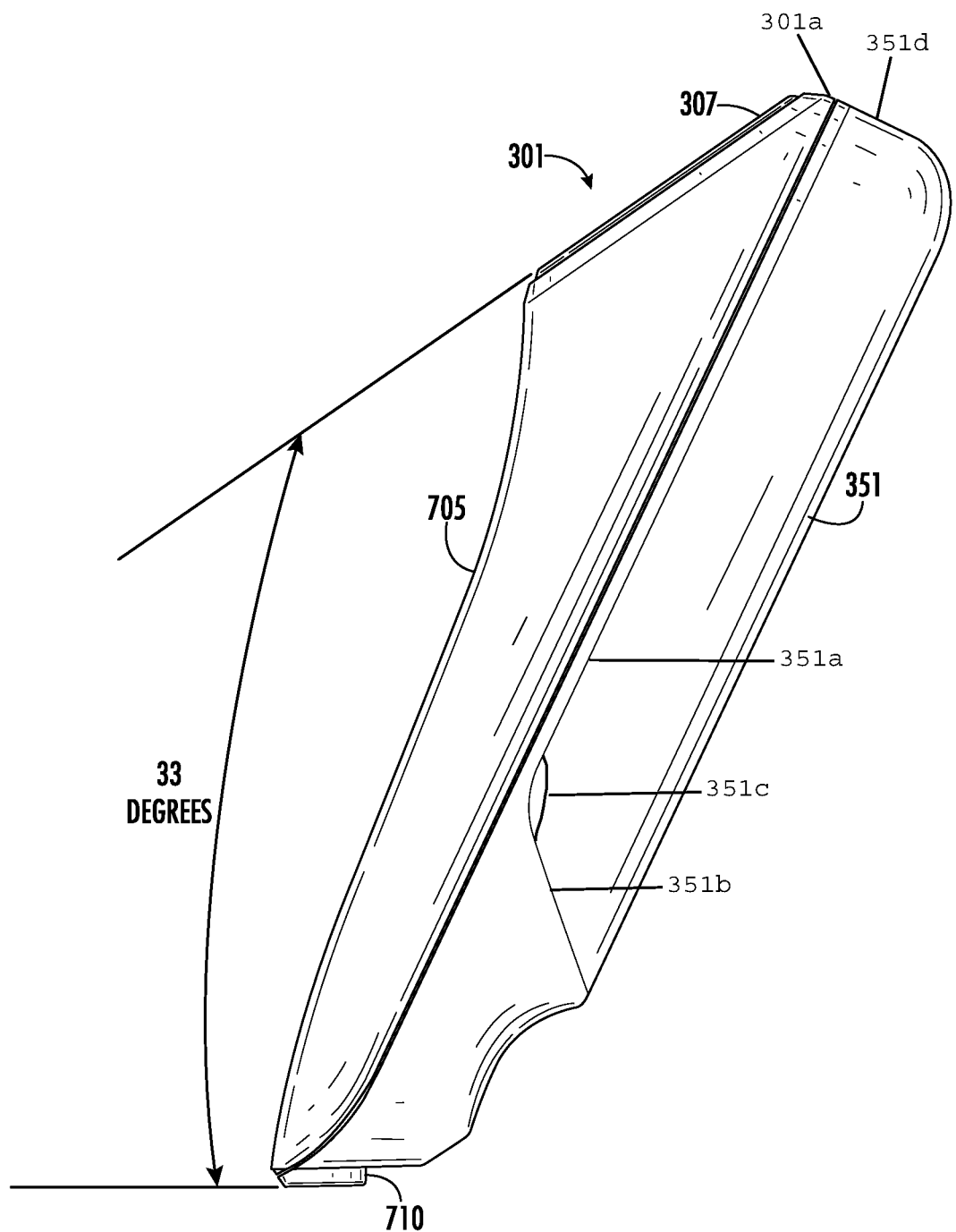
FIG. 8 shows a side view of the system unit.

FIG. 8 shows a side view system unit 301, in an implementation. The housing 705 of the system unit includes a bezel 710 that houses a portion of the probe tip. The bezel includes an opening the exposes a probe face of the probe tip.

The side view shows the angle between the display of the system unit from the side view and the probe face of the probe tip of the system unit from the side view. The angle may be from about 25 degrees to about 37 degrees. In an implementation, the angle is about 33 degrees. When the probe face faces patent tissue (such as from inside the sheath) or contacts patient tissue (such as when the system unit is used without the sheath) and oriented approximately parallel to a horizontal surface, such as an operating table, a gurney, the ground, or another horizontal feature, the display is directed upward for easy viewing by a user holding the sheath or system unit in their hand. For example, when the back of the sheath or the back of the system unit is held against the webbing of skin (i.e., the purlicue) between the index finger and thumb, the display is directed upward for easy viewing by the user holding the sheath or system unit.

Additionally, the center of mass of the battery of the system unit is over a user's hand when the sheath or system unit is held against the webbing of skin (i.e., the purlicue) between the index finger and thumb. With the center mass over a user's hand, the sheath with the system unit inside is relatively easy to maneuver across patient tissue with relatively fine dexterity so that the second window can be easily placed onto to target locations on the tissue, with relatively uniform pressure of the second window on a target location, and without fatigue so that the uniform contact and uniform pressure remains between the second window and the tissue when the system unit is taking oximetry measurements. That is, the angular geometry and the center of mass of the system unit and sheath facilitates the system unit making reliable oximetry measurements.

Figure 9A:
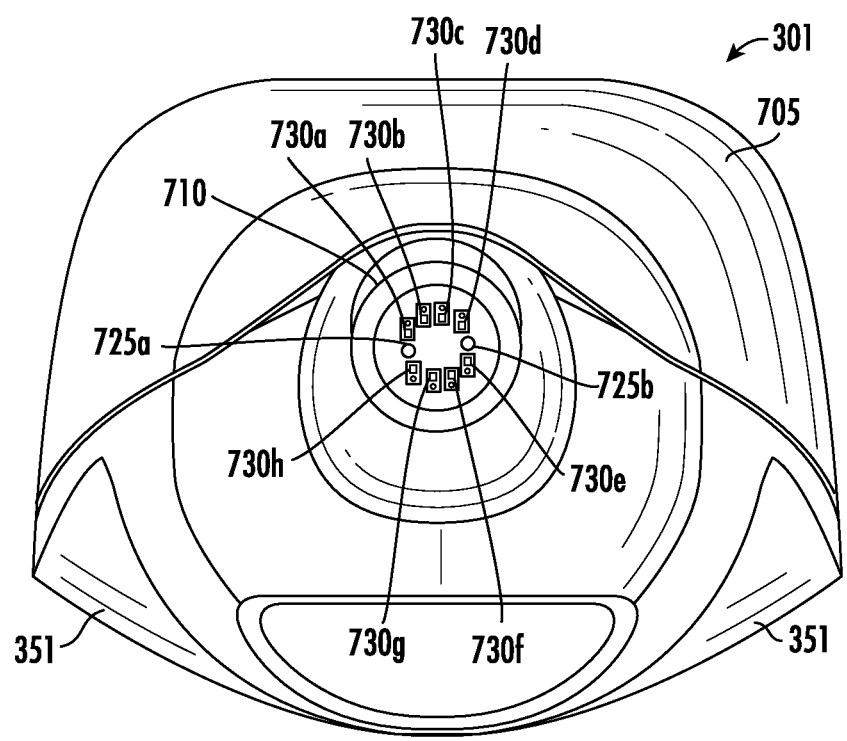
FIG. 9A shows an end view of the system unit.

FIG. 9A shows an end view of the second end of the system unit, in an implementation. The end of bezel 710 is shown with the probe face 715 in the opening of the bezel. The probe face may include an aperture plate 720 that includes a number of source apertures, for example, source apertures 725a and 725b, and includes a number of detector apertures 730a-730h. Each of the source apertures may be included in a source structure that may include light sources, such as one or more optical fibers, laser diodes, LEDs, one or more portions of the aperture plate, or other structures at the probe tip in any combination. Each of the detector apertures may be included in a detector structure that may include light detectors, such as one or more optical fibers, photodetectors, one or more portions of the aperture plate, or other structures at the probe tip in any combination.

Figure 9B:
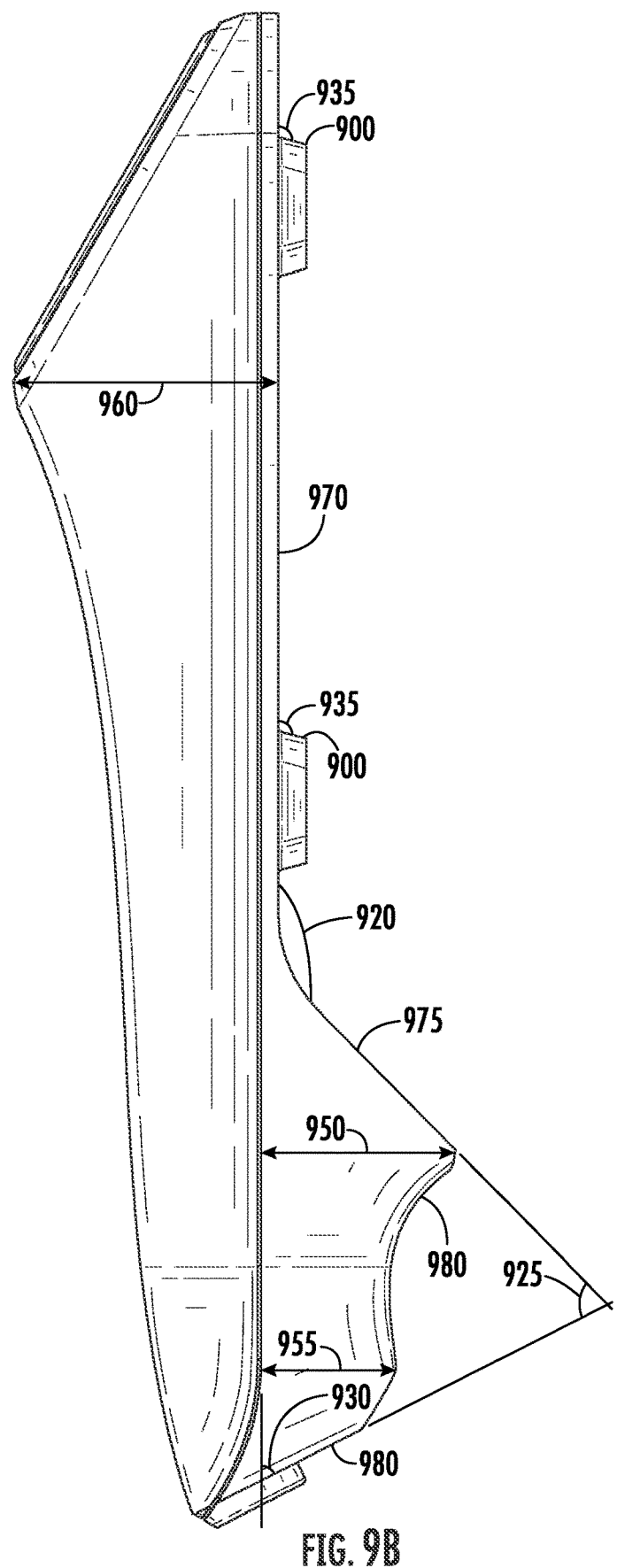
FIG. 9B shows a side view of the system unit without the battery attached to the system unit.
Figure 9C:
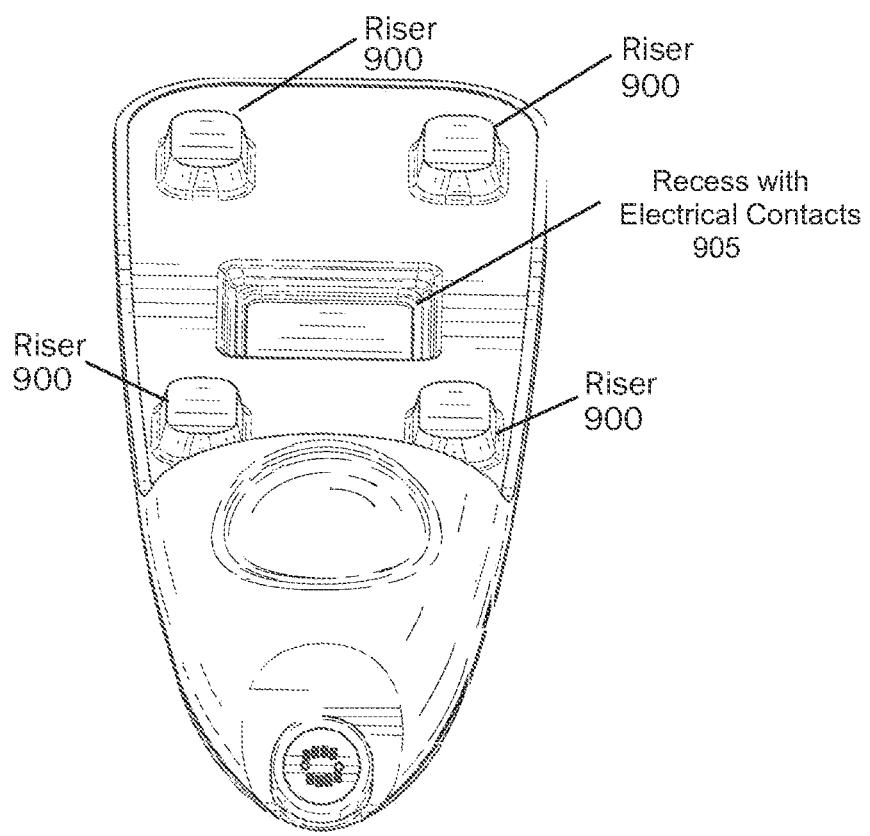
FIG. 9C shows a back view of the system unit without the battery attached to the system unit.

FIGS. 9B-9C show a side view and a back view of the system unit without the battery attached to the system unit. The bottom surface of the system unit includes a number of risers 900 (e.g., four risers). The risers may have sidewalls that are sloped with respect to the bottom surface of the system unit. The angle 935 between the sidewalls of the risers and the bottom surface of the system unit may be from about 90 degrees to about 150 degrees. In an implementation, the angles may be from about 100 degrees to about 110 degrees. In an implementation, the angles may be from about 105 degrees to about 110 degrees. In an implementation, the angles may be from about 107 degrees to about 108 degrees. In an implementation, the angles may be from about 106 degrees to about 107 degrees. In an implementation, the angles may be from about 108 degrees to about 109 degrees. In an implementation, the angles may be from about 105 degrees to about 106 degrees. In an implementation, the angles are not acute angles.

The risers may include magnets that magnetically couple to corresponding located metal pieces or magnets in the battery housing. The risers may include metal pieces that magnetically couple to corresponding located magnets in the battery housing. The bottom surface of the battery housing may have corresponding located pockets that receive the risers. The pockets may have sloping sidewalls that contact the sidewalls of the risers when the battery is connected to the system unit.

In an implementation, the backside of the system unit includes a number of surfaces that have a number of angular orientations with respect to each other. For example, surface 970 and surface 975 are angle by an angle 920 with respect to each other. Angle 920 may be from about 90 degrees to about 150 degrees. In an implementation, the angle may be from about 130 degrees to about 140 degrees. In an implementation, the angle may be from about 135 degrees to about 140 degrees. In an implementation, the angle may be from about 137 degrees to about 138 degrees. In an implementation, the angle may be from about 136 degrees to about 137 degrees. In an implementation, the angle may be from about 138 degrees to about 139 degrees. In an implementation, the angle may be from about 135 degrees to about 136 degrees (e.g., about 135.5 degrees). In an implementation, the angles are not 180 degrees (i.e., a straight angle) or larger than 180 degrees (i.e., a reflex angle).

The battery 351 includes side surfaces 351a and 351b (FIG. 8) that respectively connect to side surfaces 970 and 975 of the system unit when the battery is attached to the system unit. Angle 351c of the battery is approximately equal to angle 920 of the system unit.

Figure 20:
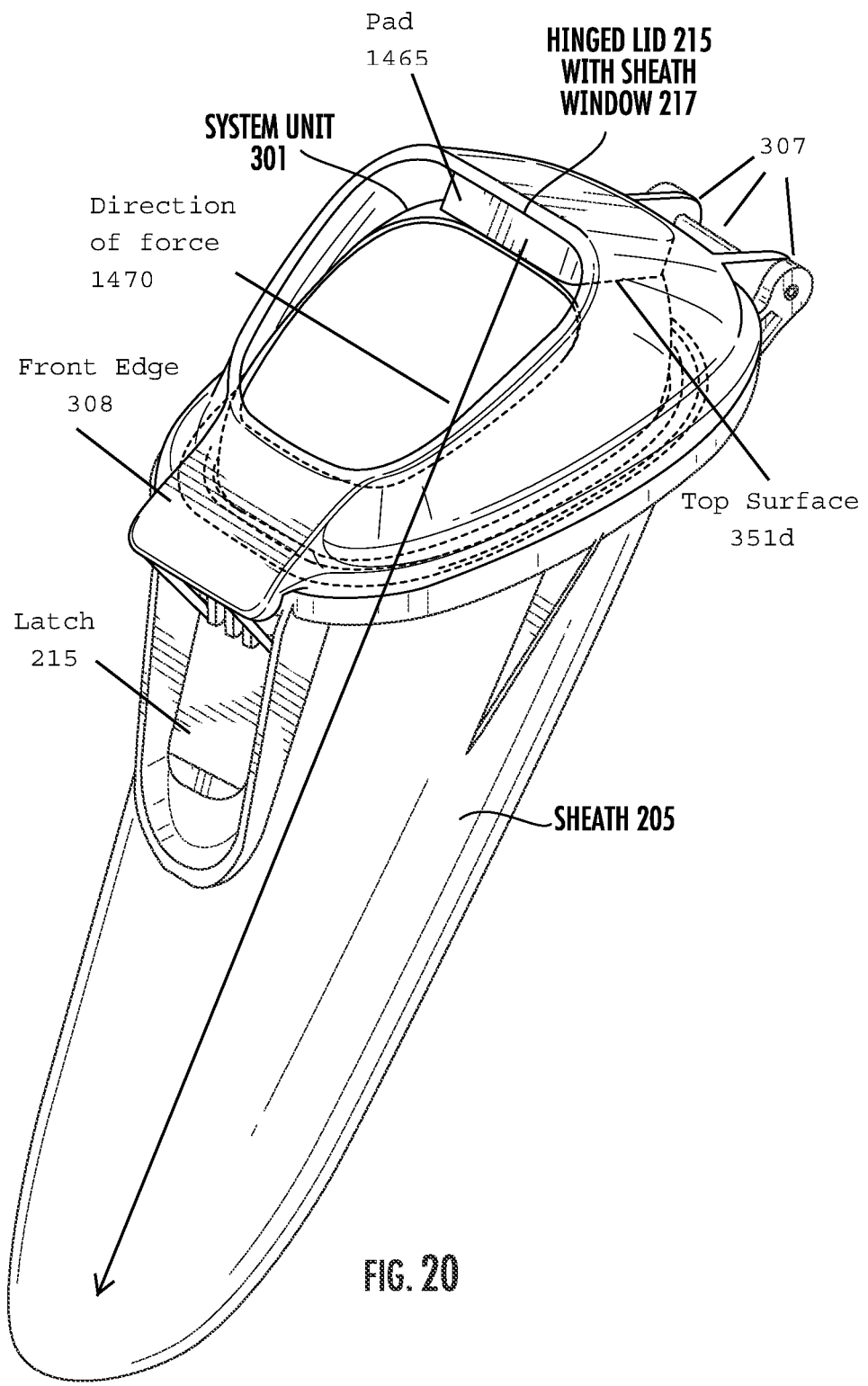
FIG. 20 shows a perspective view of the sheath, system unit, and power block, in an implementation with the lid of the sheath closed on the base of the sheath.

In an implementation, when the system unit is placed into sheath 205 as shown in FIG. 20 with lid 215 of the sheath closed onto bottom portion 220 (e.g., body) of the sheath, pad 1465 places a force on the top surface of the battery housing, the top surface of the system unit, or both in a direction toward the sheath window 218. Thus, the pad places a force that is transferred to the probe face of the probe tip of the system unit to the inner surface of sheath window 218. The force allows for the probe face and inner surface of the sheath window to stay in contact while the system unit is used to make oximetry measurements. The force is sufficient so that the probe face and inner surface of the sheath window will not come out of contact when the sheath is oriented upward (e.g., upward with respect to the downward force of gravity of the earth).

Figure 9D:
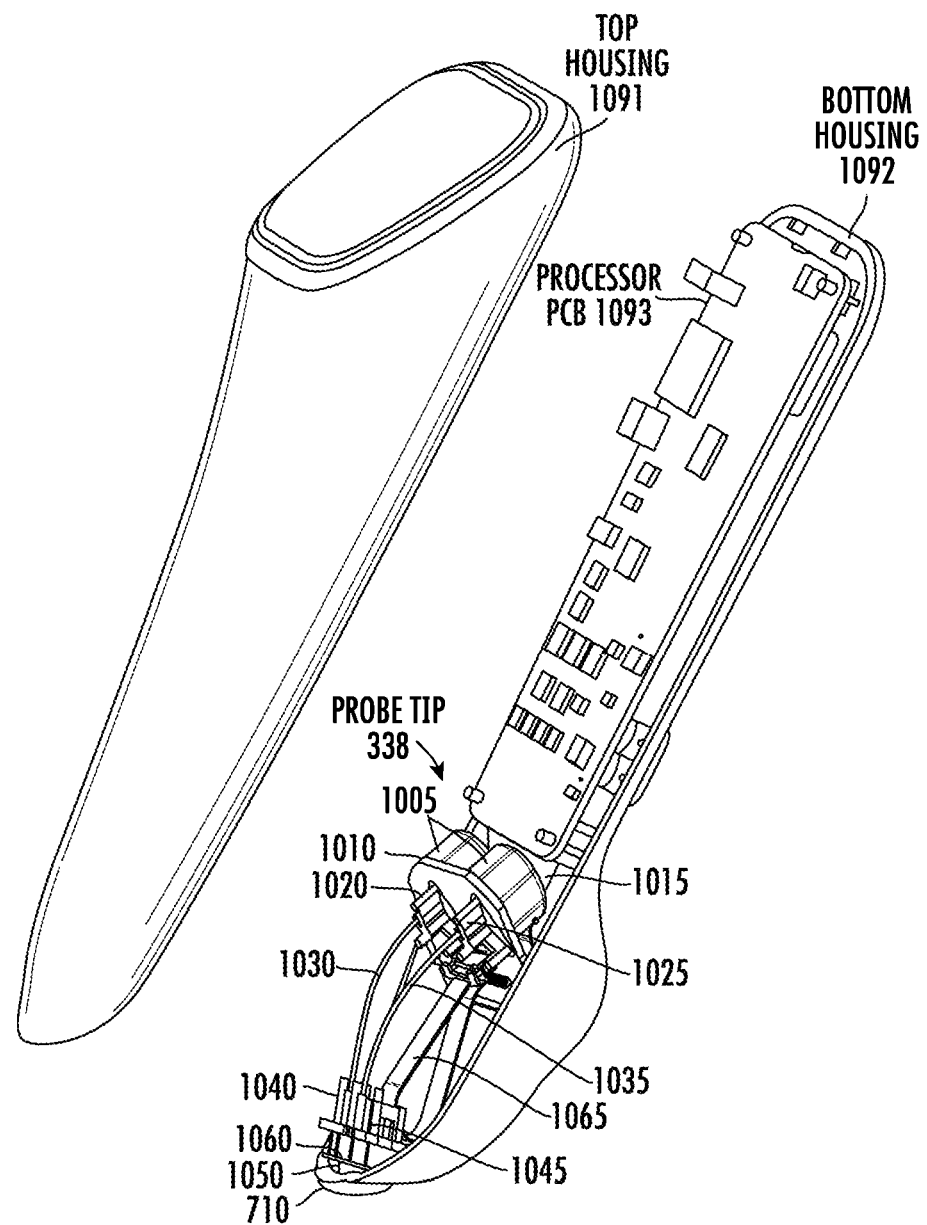
FIG. 9D shows a view of the system unit with a top housing of the system unit separated from a bottom housing of the system unit.

In an implementation, where the force from the pad is applied to the top surface 351d of the battery housing, the battery transfers the applied force on the battery to the system unit. The battery can transfer the applied force from surface 351b of the battery to surface 975 of the system unit. Because angle 351c and angle 920 are not straight angles or reflect angles, the force transfers. Further, where one or more beveled surfaces 351e of pockets in the battery are connected to corresponding beveled surfaces 900 of the risers 900 or a pocket 905 (FIG. 9C) of the system unit, the battery can transfer the force to the system unit through these surfaces. In an implementation, pocket 905 is an aperture that exposes electrical contacts formed on the backside of a PCB 1093 of the system unit (FIGS. 9C-9D). The front side of PCB 1092 is shown in FIG. 9D and the backside of the PCB faces towards the upper back wall of the bottom housing 1092 of the sheath. The electrical contacts can include battery contacts through which the battery transfer electrical current to the system unit and can include data contacts where the battery and system unit can transfer data, such as an encrypted identifier of the battery. In an implementation, the battery contacts includes two electrical contacts, namely a power contact and a ground contact. The data contact includes an information contact and shares the ground contact with the electrical contacts).

In an implementation, where the sheath and battery have a straight angle or reflex angle 920 and 351c, the force supplied from the battery back from surfaces 351e to the system unit at the risers 900 is sufficient for the probe face and inner surface to contact for use. With the combination of forces between surfaces 975 and 351b and between the riser 900 and surfaces 351e, the force applied across the probe face and inner surface may be relatively more uniform than if forces are only supplied by the risers 900 and surface 351e. Uniform pressure allows for the refractive index at the interface between probe face and inner surface to be more uniform and allow for the light from the system unit to be uniformly transmitted from the probe face and through the sheath window 218 to tissue of a patient allowing for more accurate oximetry measurements.

In an implementation, the pad has a first elasticity, the lid of the sheath has a second elasticity, and the body of the sheath has third elasticity. The first elasticity is more elastic than the second elasticity and the third elasticity. The first elasticity may be in the OO durometer scale of the Shore durometers and the second and third elasticities may be in the D durometer scale of the Shore durometers. The OO scale is used for softer materials than the D scale is used for harder materials. The pad may have a Shore durometer from about 0045 to about 0055 in the OO scale. The lid may have a Shore durometer of about D80. The body may have a durometer of about 90.

The foam may be neoprene, polyethylene, cross-linked polyethylene, polyurethane, reticulated polyurethane, melamine, or another type of foam.

The lid of the sheath is a plastic material. The material can be polycarbonate, acrylic, polyethylene terephthalate (PET), PETG, polyester, acrylonitrile butadiene styrene (ABS), or other plastic material. Polycarbonate, for example, is a material the lid may be made of because the material is easy to form, can be transparent, can be easily polished, and can be sterilized by a variety of sterilization techniques and material, such as ethylene oxide (EtO), exposed to irradiation (both gamma and electron-beam), and steam autoclaving, isopropyl alcohol exposure, and other techniques and materials.

The body of the sheath is a plastic material. The material can be polycarbonate, acrylic, polyethylene terephthalate (PET), PETG, polyester, acrylonitrile butadiene styrene (ABS), or other plastic material. ABS, for example, is a material the body may be made of because the material is easy to form and can be sterilized by a variety of sterilization techniques and material, such as ethylene oxide (EtO), exposed to irradiation (both gamma and electron-beam), and steam autoclaving, isopropyl alcohol exposure, and other techniques and materials. In an implementation, the body of the sheath is metal. In an implementation, the body of the sheath is ceramic.

Because the foam is more elastic than the lid and body, the foam can compress and the force applied by the foam to the system unit (e.g., when the lid is closed, FIG. 20) is a spring force with a relatively low spring constant. Because the lid and body have low elasticities, the lid and body do not deform when the foam applies a force to the system unit when the lid is closed. Deformation of the lid or body could allow the sheath to leak, which is not desirable. Thus, the material for the lid and body are selected to have the described elasticities (e.g., lower than the foam) so that these elements do not deform when the system unit is in the sheath and the lid is closed.

In an embodiment, the pad can be a linear spring that behaves according to Hooke's Law, sometimes referred to as Hooke's Law of Elasticity. The force of a spring, such as a linear spring, is given by:

$$F = -kx \quad (1)$$

Hooke's Law is an approximation that states the extension of a spring is in direct proportion with the load added to it as long as this load does not exceed the elastic limit. Above a certain stress or force which may be referred to as the elastic limit or yield strength of an elastic material, the solid (e.g., the spring) may deform irreversibly, exhibiting plasticity. Generally, the forces discussed in this application applied to the pad to compress the pad will be within the elastic range (not plastic range) of the pad. In other implementations, the forces will exceed the elastic range of the pad.

In an implementation, the latch is metal and applies a spring force to hold the lid closed to the body and thus applied a spring force in series with the pad to the system unit when the lid is closed and the latch is latched. The spring constant of the latch may be higher than the spring constant of the pad.

In an implementation, the pad is positioned closer to the hinge 207 of the sheath than the front edge 308 or latch 215 of the sheath. The front edge, latch, and other portions of the lid allow a relatively large torque to be applied to the lid when the lid is closed and latch so that the force applied by the pad onto the system unit is mechanically leveraged. The mechanical leverage (i.e., mechanical advantage) allows for the force applied by the pad to the system unit, and thus the for applied by the probe face to the inner surface of the sheath window, to be sufficient so that the probe face and inner surface contact and do not come out of contact during use.

The torque or moment of a force with respect to a point is:

$$m = Fd \quad (2)$$

where F is the force applied at a distance d from the point. In an implementation, distance d is a length of the offset or lever arm.

As one of skill in the art will recognize, variables such as the spring constant, the length of the lever arm of the lid and hinge, number of springs, arrangement of springs (e.g., springs in parallel and springs in series), and combinations of these can be varied to produce a desired pressure at the probe face on the inner surface of the sheath window 218 of the system unit so that the probe face and inner surface contact so that they do not come out of contact during use of the sheath and system unit when making oximetry measurement. Thus, the oximetry measurements can be reliable.

Factors that may contribute to the spring constant of the first spring (e.g., pad) and the second spring (e.g., latch) include the springs' dimensions such as the springs' length, width, or thickness, shape or cross-sectional shape of the spring which can affect a moment of inertia, the material that the spring is made of (e.g. plastic or metal), or combinations of these.

An implementation may include two or more springs in series (e.g., springs linked end-to-end), two or more springs in parallel (e.g. springs side-by-side), or a combination of springs in series and springs in parallel. For springs in parallel, the equivalent spring constant of the combination is a sum of the spring constants of each individual spring. For springs in series, to find the equivalent spring constant of the combination, add the reciprocals of the spring constants of each individual spring and take the reciprocal of the sum.

FIG. 9D shows a view of the system unit with a top housing 1091 of the system unit separated from a bottom housing 1092 of the system unit. This figure shows a PCB 1093 on which various circuits of the system unit are mounted, such as the processor 304, volatile memory 312, nonvolatile memory 315, human interface device (HID) 319, input-output (I/O) interface 322, network interface 326, and accelerometer 332.

The probe tip 338 is attached to a lower portion of the bottom housing. The probe tip may be connected to the bottom housing by mechanical fasteners, an adhesive (e.g., an glue, such as epoxy glue), another device, or any combination of these features. The probe tip includes two reflector domes 1005, an LED PCB 1010, a first optical fiber holder 1020, a second optical fiber holder 1025, a third optical fiber holder 1040, a fourth optical fiber holder 1045, a first optical fiber 1030, a second optical fiber 1035, a first PCB 1050, a second PCB 1060, a first ribbon cable 1015, and a second ribbon cable 1065. In an implementation, a wire (e.g., a ribbon cable) couples the display located in the top housing 1091 to the PCB 1093 that is connected to the bottom housing. PCB 1093 may be elevated above a back surface of the bottom housing so that the PCB is in the inner space of the upper housing when the upper and lower housing are connected to form the system unit.

In an implementation, the top housing and bottom housing are coupled by an adhesive, such as an adhesive tape. The tape may be a very high bond (VHB) tape, such as VHB tape produced by 3M Corporation of Saint Paul, Minnesota. The VHB tape provides a seal that fluid cannot penetrate at standard atmospheric pressure at sea level. In an implementation, the display is adhered to the upper housing with VHB tape.

In an implementation, angle 925 between surface 975 and surface 980 is an acute angle from about 60 degrees to about 80 degrees. In an implementation, angle 925 is from about 70 degrees to about 80 degrees. In an implementation, angle 925 is from about 70 degrees to about 75 degrees. In an implementation, angle 925 is about 70 degrees. In an implementation, angle 925 is about 71 degrees. In an implementation, angle 925 is about 72 degrees or about 72.5 degrees. In an implementation, angle 925 is from about 73 degrees. In an implementation, angle 925 is from about 74 degrees. In an implementation, angle 925 is from about 75 degrees.

In an implementation, angle 930 between surface 970 and surface 980 is an acute angle from about 55 degrees to about 75 degrees. In an implementation, angle 925 is from about 60 degrees to about 70 degrees. In an implementation, angle 925 is from about 60 degrees to about 65 degrees. In an implementation, angle 925 is about 60 degrees. In an implementation, angle 925 is about 61 degrees. In an implementation, angle 925 is about 62 degrees. In an implementation, angle 925 is about 63 degrees. In an implementation, angle 925 is about 64 degrees. In an implementation, angle 925 is about 65 degrees.

In an implementation, the length 950 of the housing from surface 970 to the outer surface along a perpendicular line from surface 970 is longer than the length 955 of the housing from surface 970 to the outer surface along a perpendicular line from surface 970. In an implementation, the length of line 960 is the longest transverse length of the housing from surface 970. Length 970 is from about 25 millimeters to about 35 millimeters. In an implementation, length 970 is about 30.4 millimeters. Length 950 is from about 15 millimeters to about 25 millimeters. In an implementation, length 950 is about 21 millimeters. Length 955 is from about 10 millimeters to about 15 millimeters. In an implementation, length 955 is about 14 millimeters.

Figure 10A:
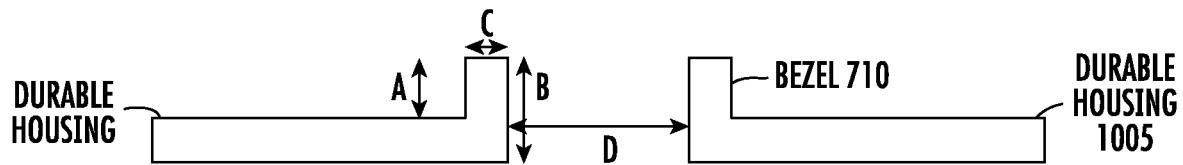
FIGS. 10A-10D show a number of steps for forming the probe face of the probe tip and forming the finished bezel of the housing of the system unit.

FIGS. 10A-10D show a number of steps for forming the probe face 715 of the probe tip 338 and forming the finished bezel 710 of the housing 1005 of the system unit 301. FIG. 10a shows the bezel 710 of the housing 1005 at an initial height A where the height is from the outside surface of the housing to the top of the bezel. Height A may be from about 3.5 millimeters to about 4 millimeters. In a specific implementation, height A is about 3.75 millimeters. The inner height B of the bezel is from the inside surface of the housing to the top of the bezel. Height B may be from about 4.5 millimeters to about 5.5 millimeters. In a specific implementation, height B is about 5.05 millimeters. The diameter D of the opening of the bezel may be from about 8 millimeters to about 10 millimeters. In a specific implementation, the diameter of the opening of the bezel may be about 9.1 millimeters. The width C of the bezel at the bezel's end may be about 1.0 millimeters to about 2.0 millimeters. The width C may vary around the circumference of the bezel. In a specific implementation, the width C of the bezel is about 1.5 millimeters.

Figure 10B:
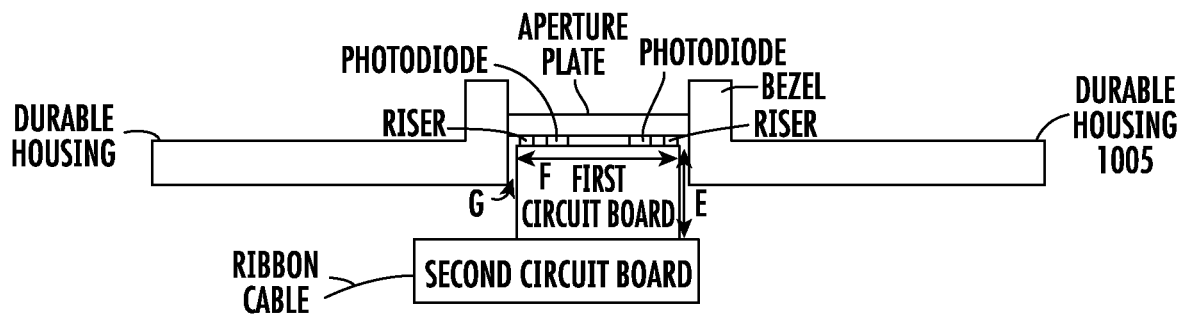

FIG. 10B shows the housing and bezel with a portion of the probe tip 338 in the housing and bezel. The portion of the probe tip shown includes a first circuit board 1020, a second circuit board 1025, riser 1030, photodiodes 1035, an aperture plate 1040, and a ribbon cable 1045 connected to the second circuit board. The ribbon cable can transmit electrical signals for the sources and detectors and may transmit temperature information from one or more temperature sensor located adjacent to the sources. The first and second circuit boards may include electrical traces that are coupled. The second circuit board may be a fiberglass circuit board (e.g., FR4) that includes electrical traces that are connected to electrical traces of the first circuit board. The electrical traces of the first circuit board may extend upward from the second circuit board along the outer surface of the first circuit board. The first and second circuit boards may be connected by mechanical fasters, plastic welding, an adhesive (e.g., epoxy), another material, or any combination of these materials. The first circuit board may have a diameter F of about 6 millimeters to about 8 millimeters. In a specific implementation, the diameter F of the first circuit board is about 7 millimeters. The first circuit board may have a height E of about 3 millimeters to about 4 millimeters. In a specific implementation, the height E of the first circuit board is about 3.5 millimeters.

A distance G between the side of the first circuit board and the inner sidewall of the bezel may be about 0.5 millimeters to about 1.5 millimeters. In a specific embodiment, the distance between the side of the first circuit board and the inner sidewall of the bezel may be about 1.05 millimeters.

The riser may be connected to both the first circuit board and the aperture plate and may separate the first circuit board and aperture plate may be predetermined height. The photodiodes may be mounted on a top surface of the first circuit board and be connected to the electrical traces of the first circuit board. The aperture plate may include an aperture for each photodiode that is mounted on the first surface of the first circuit board and the diodes may respectively be inside the apertures. The height of each riser may be about 100 micrometers to about 200 micrometers. In an implementation, the height of each riser is about 150 micrometers.

Figure 10C:
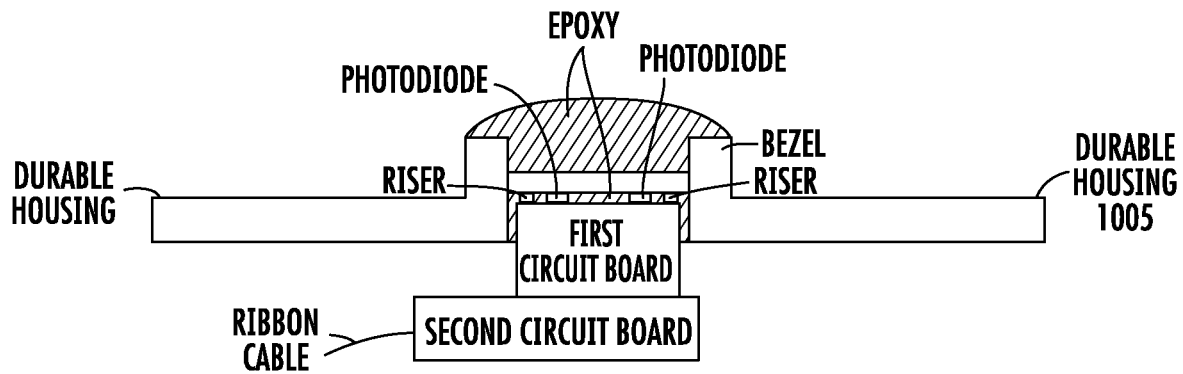

After the portion of the probe tip shown in FIG. 10B is placed into the opening of the bezel, epoxy is flowed into the opening as shown in FIG. 10C. The epoxy may flow into the apertures of the aperture plate, along the sides of the first circuit board, and may flow to the second circuit board and around the sides of the second circuit board.

Figure 10D:
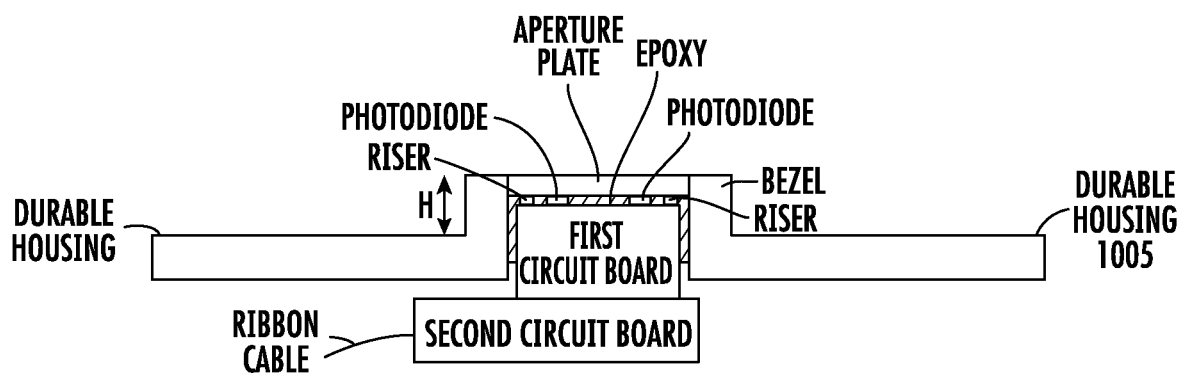

After the epoxy cures, the epoxy and a portion of the side of the bezel may be removed (e.g., polished thinner) to a final height, as shown in FIG. 10D. The final outside height H of the bezel may be about 2.0 millimeters to about 3 millimeters. In a specific implementation, the final outside height H of the bezel is about 2.58 millimeters. In an implementation, a portion of the aperture plate may also be thinned (e.g., polished thinner) when the bezel is thinned and epoxy are removed. The aperture plate can include a marker embedded in the plate. The embedded marker is exposed and polished away in the polishing process, the polishing is completed when the marker is polished away.

In an implementation, the epoxy is polished down so that a layer of epoxy covers the surface of the aperture plate. In an implementation, the epoxy is polished down to the surface of the tops of the photodetectors inside the apertures of the aperture plate. In another implementation, a thin layer of epoxy remains over the tops of the photodiodes after polishing.

In an implementation, the aperture plate is in the opening of the durable housing 1005 and is not in the bezel. In an implementation, a portion of the first circuit board is in the opening of the durable housing 1005 and is not in the bezel. In an implementation, the first circuit board is not in the opening of the durable housing 1005. The epoxy and bezel are polished down the outer surface of the durable housing such that the probe face of the probe tip is flush with outer surface. After polishing, a layer of epoxy is over the aperture plate when the aperture plate is located in the opening in the durable housing. The layer of epoxy may be from about 5 micrometers to about 50 micrometers.

In an implementation a layer of epoxy is over the bezel sidewall and the front surface of the aperture plate. The layer of epoxy may be from about 5 micrometers to about 50 micrometers. In an implementation where the top surface of the aperture plate is in the sidewall of the durable housing after polishing, a layer of epoxy is in the opening in the sidewall and over the front surface of the aperture plate that faces outward from the sidewall. The layer of epoxy may be from about 5 micrometers to about 50 micrometers.

Figure 11:
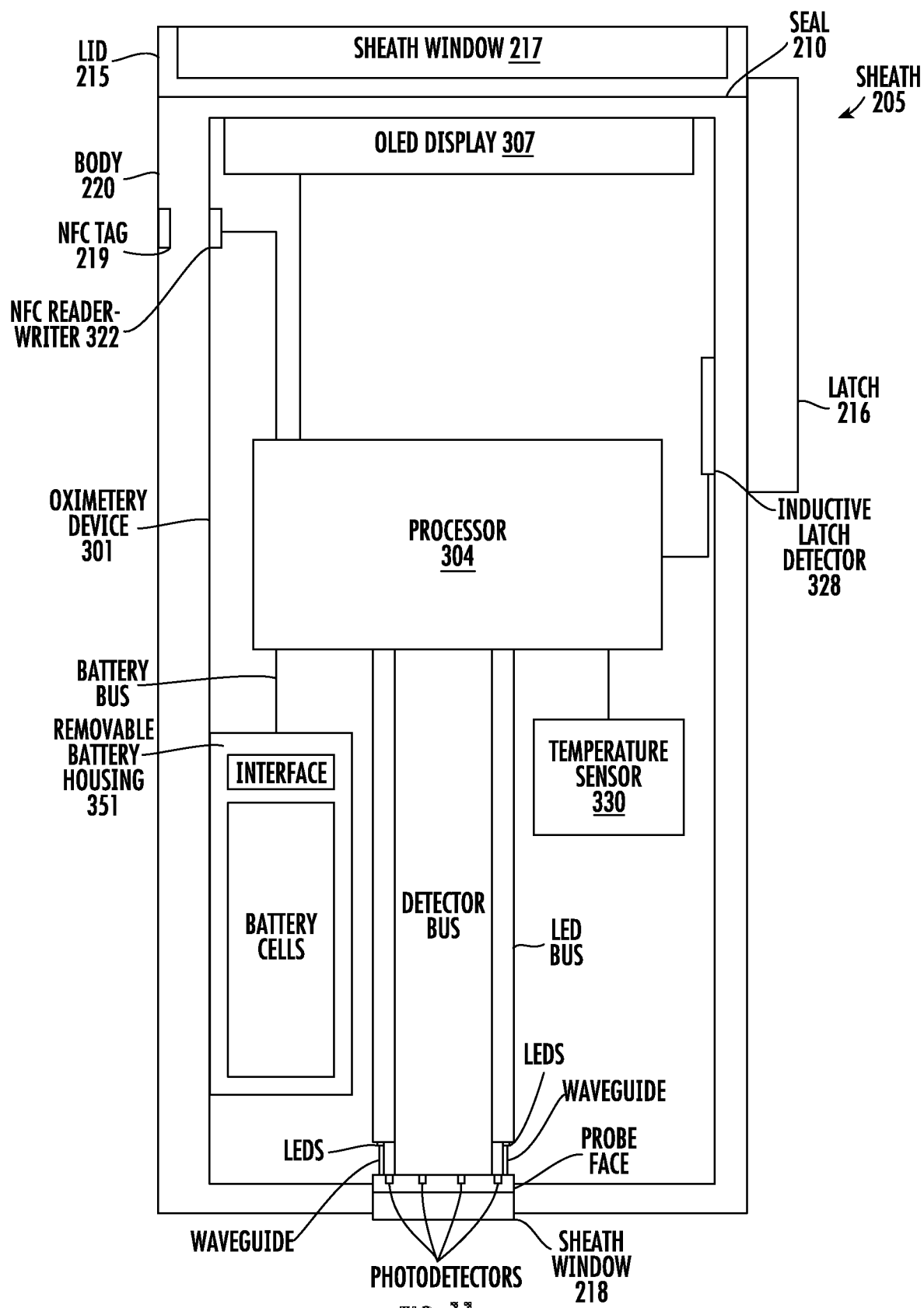
FIG. 11 is a block diagram of the system unit in a sheath, in an implementation.

FIG. 11 is an additional block diagram of system unit 301 in sheath 205, in an implementation. The block diagram shows a general structure of the sheath, system unit, and elements included in these device. The elements included in the devices can be positioned at alternative locations, orientations, or both. The sheath includes the seal 210, the lid 215, the body portion 220, a latch 216, a first sheath window 217, a second sheath window 218, and a radio-frequency communication device 219, such as an NFC tag. The sheath may include a hinge that hinge couples the lid to the body portion and allows the lid to be opened and closed. Both the lid and sheath can be formed of a relatively rigid plastic material.

As described above, the latch latches that lid closed and seals the seal. The latch also releases the lid from the closed position and allows for the seal to be unsealed. The latch detector 328 (e.g., an inductor or a capacitive detector and an A-to-D converter coupled to the processor) of the system unit is positioned nearest to the latch when the latch is closed (i.e., the first distance from the latch detector) so that the latch detector can detect when the latch is latched, the lid is closed, and the seal is sealed. That latch detector can detect when the latch opens and moves away from the first distance.

In an implementation, a first portion of the latch is rigidly connected to the lid and a second portion of the latch extends in a cantilever configuration from the lid. The first and second portions are opposite portions of the latch. The latch is capable of bending to latch that latch to the body of the sheath and bending to unlatch the latch from the body. The latch can be steel, such as spring steel, which allows the second portion (e.g., cantilevered portion) of the latch to bend to latch and unlatch the latch from the body.

In an implementation, a first portion of the latch is rigidly connected to the body and the second portion of the latch extends in a cantilever configuration from the lid. The latch capable of bending to latch that latch to the lid of the sheath and unlatch the latch from the lid.

The latch can be hinge connected to the lid via a lid hinge. With the lid hinge connected to the lid, that latch can rotate towards the body of the sheath and away from the body of the sheath to latch that latch to the body and unlatch the latch from the body. In another implementation, the latch is hinge connected to the body of the sheath and can rotate towards the lid and away from the lid to latch to the lid and unlatch from the lid.

In an implementation, the first window 217 is located in the lid of the sheath. The first window is positioned over the display 307 (e.g., an organic LED display) of the system unit when the lid of the sheath is closed. The first window can be transparent so that information displayed on the display is visible and discernable to a user when the lid of the sheath is closed. The first window can be a plastic material or glass. The first window can be sealed to the lid via an adhesive, such as epoxy, an O-ring, welding, heat-stake (if both materials are plastic), or another seal material. The seal can prevent contaminants (e.g., patient tissue, patient fluid, or other debris) from passing through the seal and contaminating the system unit. The sheath window may be a square-shaped window or a rectangular window that approximately matches the size and shape of display 307.

The second window 218 can be at an opposite end of the sheath from the first window. The second window can contact the probe face of the probe tip when the system unit is in the sheath. The second window can have a relatively flat surface that contacts the polished probe face so that relatively little air is trapped between the second widow and the probe face when the second window and probe face are in contact. In an implementation, the inside surface (e.g., inside the body of the sheath) of the second window can have an adhesive that can stick to the probe face of the system unit.

In an implementation, the I/O interface 322 of the system unit includes an NFC reader-writer. The NFC reader-writer can power the NFC tag 219 of the sheath so that the NFC reader-writer can communicate with the NFC tag. In some implementations, the NFC tag is battery powered by a battery of the NFC tag. In an implementation, the NFC tag is a read only NFC tag where information can be read from the NFC tag by the NFC reader-writer of the system unit. In an implementation, the NFC tag can be read and can be written to by the NFC reader-writer.

In an implementation, the NFC tag includes a memory (e.g., a non-volatile memory, a random access memory, or both) that can store an identifier for the sheath, store an indicator that indicates whether the sheath has been previously used or is unused, other information, or any combination of this information. The identifier for the sheath can be an unencrypted identifier or an encrypted identifier that is previously stored in the memory. An identifier can be unique to a sheath or an identifier can be used for a number of sheaths. The identifier can identify the sheath as a particular type of sheath, such as a sheath that is reusable or a sheath that is not reusable. The identifier can be stored in the memory of the NFC tag by a manufacturer.

Figure 12:
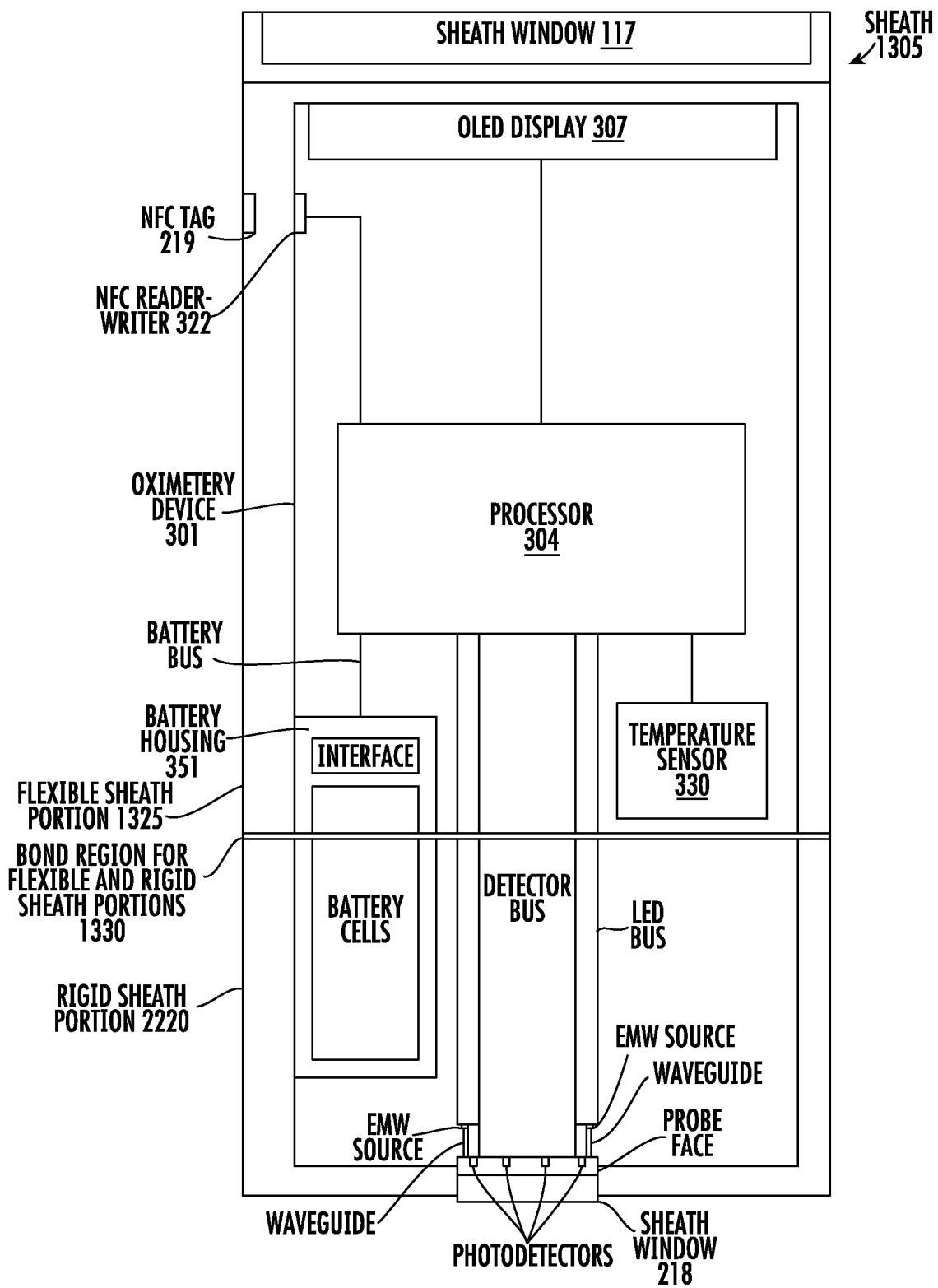
FIG. 12 is a block diagram of the system unit in the sheath, in an implementation.

FIG. 12 is a block diagram of system unit 301 in sheath 1305, in an implementation. Sheath 1205 is similar to sheath 205 but differs in that a lower body portion 1320 of the sheath is a relatively rigid plastic material and an upper body portion 1325 of the sheath is a relatively flexible plastic material. That is, the material of the upper body portion has a higher flexibility than the lower body portion. The upper and lower body portions may be coupled by an adhesive 1330, sonic welding, or another bonding material that forms a seal between the body portions. The seal is a barrier to patient tissue, patient liquid, and other contaminants. A top portion of the upper body portion can be seal so that a system unit can be sealed in the sheath where patient tissue, patient liquid, and other contaminants cannot reach the system unit when the unit is sealed in the sheath.

Figure 13:
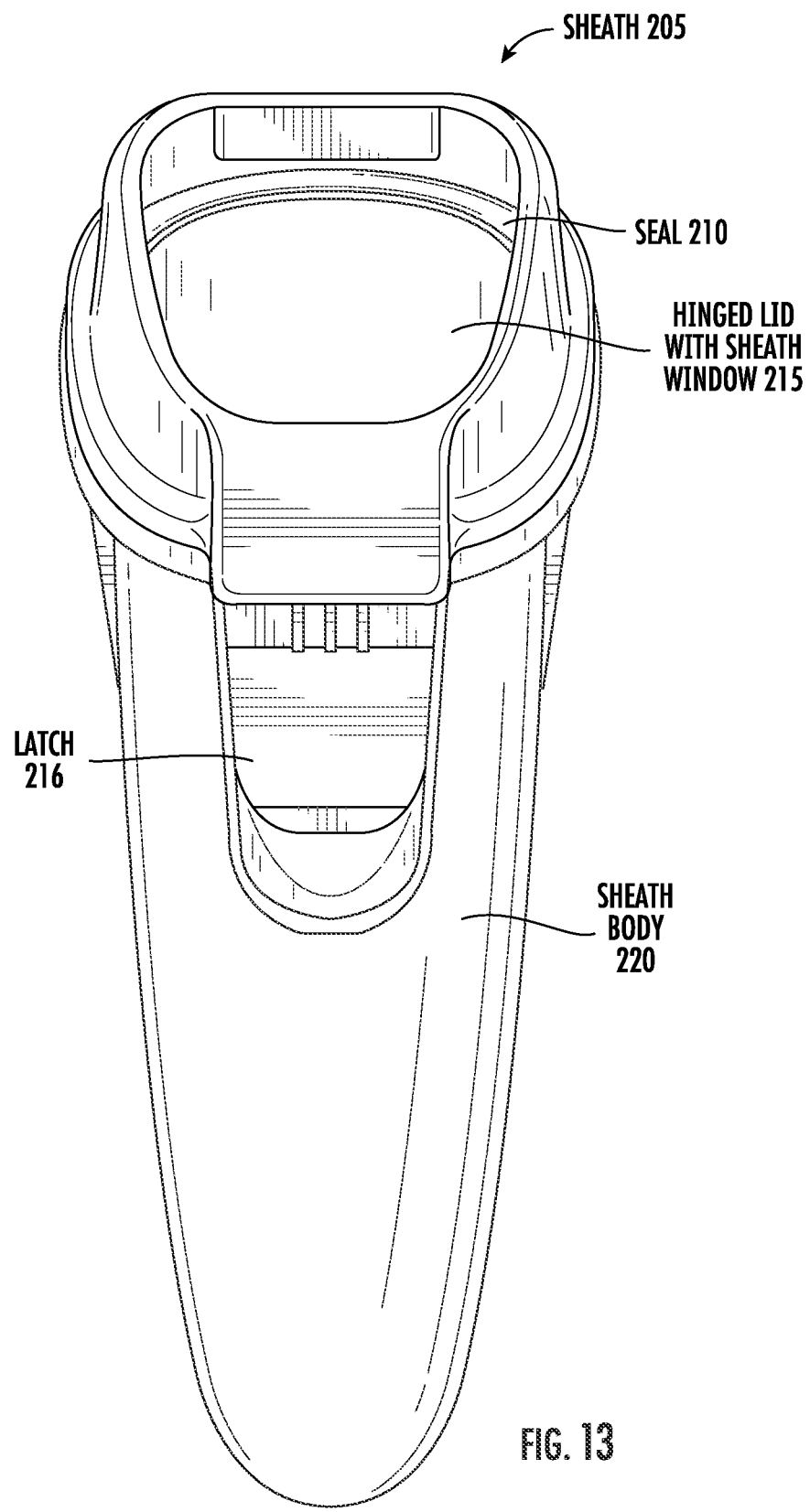
FIG. 13 shows a front view of the sheath, in an implementation.

FIG. 13 shows a front view of the sheath 205, in an implementation. The sheath is shown in FIG. 13 with the lid 215 closed against the body 220 of the sheath with the latch in a latched position against the body. The lid may be formed of a first plastic material that can be transparent (e.g., the window of the lid), translucent (e.g., portions of the lid attached to the window), opaque, or any combination of these properties. The body may be formed of a second plastic that can be transparent, translucent, opaque, or any combination of these properties. The second window of the body may be attached to the body via an adhesive (e.g., epoxy), plastic weld, or other fasteners. The second widow may form a seal with the body where the second window attaches to the body where contaminants cannot pass through the seal to contaminate a system unit in the sheath via the seal.

In an implementation, the lid of the sheath is a plastic material. The material can be polycarbonate, acrylic, polyethylene terephthalate (PET), PETG, polyester, acrylonitrile butadiene styrene (ABS), or other plastic material. Polycarbonate, for example, is a material the lid may be made of because the material is easy to form, can be transparent, and can be sterilized by a variety of sterilization techniques and material, such as ethylene oxide (EtO), exposed to irradiation (both gamma and electron-beam), and steam autoclaving, isopropyl alcohol exposure, and other techniques and materials.

The body of the sheath is a plastic material. The material can be polycarbonate, acrylic, polyethylene terephthalate (PET), PETG, polyester, acrylonitrile butadiene styrene (ABS), or other plastic material. ABS, for example, is a material the body may be made of because the material is easy to form, and can be sterilized by a variety of sterilization techniques and material, such as ethylene oxide (EtO), exposed to irradiation (both gamma and electron-beam), and steam autoclaving, isopropyl alcohol exposure, and other techniques and materials.

The second window of the sheath at the bottom of the sheath is a plastic material or a glass material. In an implementation, the window is a plastic material. The material can be polycarbonate, acrylic, polyethylene terephthalate (PET), PETG, clear polyester, clear acrylonitrile butadiene styrene (ABS), or other transparent plastic material. PET, for example, is a material the second window may be made of because the material is easy to form, can be made optically flat, can be transparent, can be relatively strong while really thin, and can be sterilized by a variety of sterilization techniques and material, such as ethylene oxide (EtO), exposed to irradiation (both gamma and electron-beam), and steam autoclaving, isopropyl alcohol exposure, and other techniques and materials. The glass can be silica, borosilicate glass, optical glass, or other types of glass, such as other types of hard glass.

Figure 14:
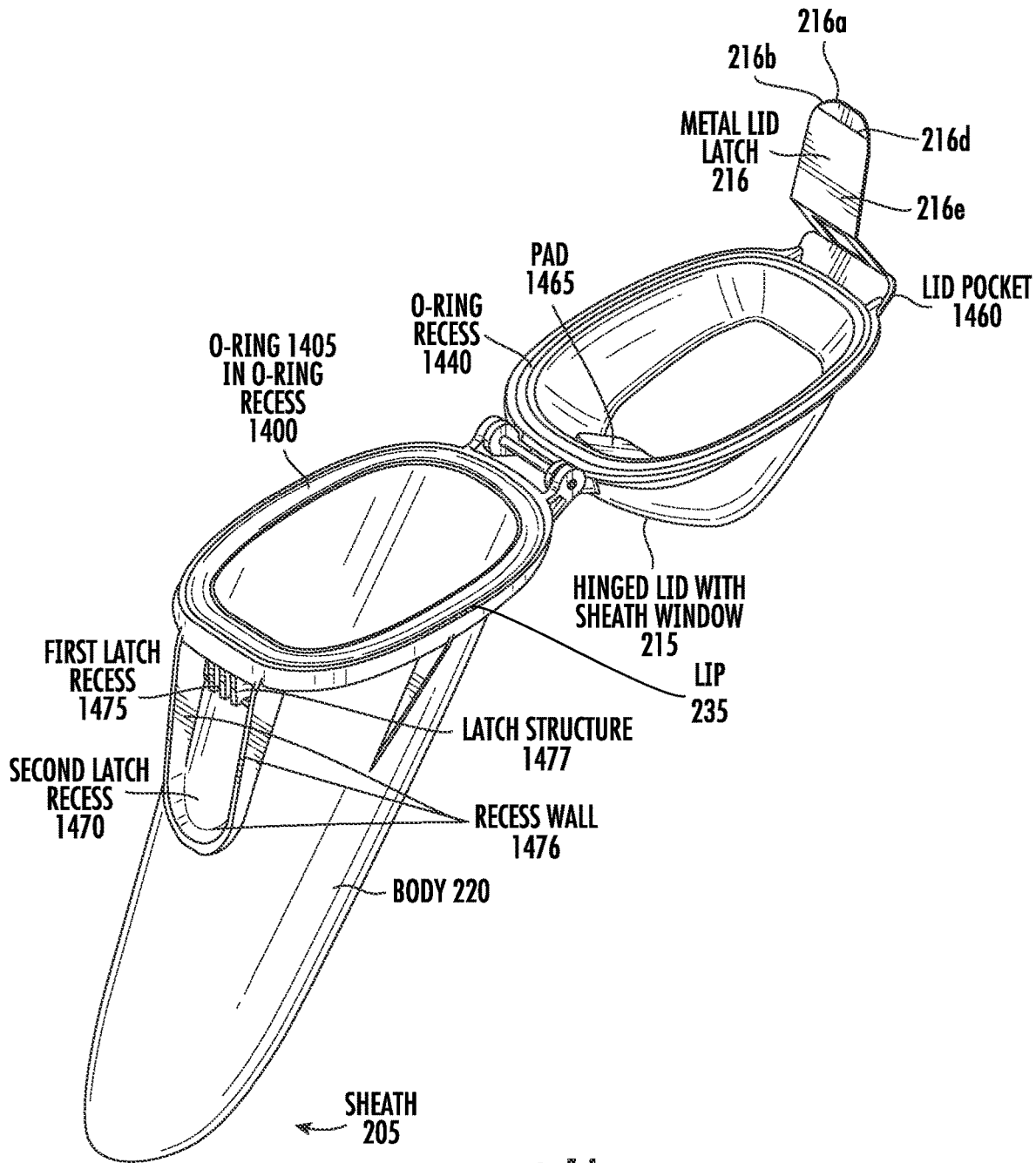
FIG. 14 shows a perspective view of the sheath, in an implementation.

FIG. 14 shows a perspective view of the sheath 205, in an implementation. The lid 215 is shown in an open position with respect to the body 220 where a system unit can be inserted into the sheath or removed from the sheath. The hinge that connects the lid and the body can be on a backside of the sheath. The body can include an O-ring recess 1400 of the top of the body. An O-ring 1405 is shown in the recess. The lid can also include an O-ring recess 4110 on the bottom of the lid. The O-ring has a diameter from 1 millimeter to about 10 millimeters. In an implementation the O-ring has a diameter of 5 millimeters. The O-ring recesses of the body and lid can contact the O-ring when the lid is closed against the body. The O-ring can form a seal that seals the lib to the body so that contaminants cannot enter the seal between the lid and body.

The O-Ring is a deformable plastic type material. In an implementation, the O-ring is medical grade silicon rubber. The Shore durometer of the O-ring may be from about 8 A to about 22 A. In an implementation, the Shore durometer of the O-ring is 15+5 A. Shore durometer values are based on a unitless scale that ranges from 0 to 100. The Shore "A" durometers traditionally designates are typically used for softer materials and range broadly enough to cover flexible rubbers up to semi-rigid plastics with almost no flexibility. In contrast, Shore "D" durometers are typically used for harder materials, such as hard rubber, semi-rigid plastics and hard plastics. The deformable nature of the material that the O-ring is formed from facilitates the ridges 1420 and 1425 being able to form trenches in the O-ring when the O-ring is compressed allowing for a biological seal of the system unit in the sheath. In an implementation, a hermetic seal is formed. The O-ring may be translucent or clear silicone rubber so that the color of the O-ring is not a distracting during use.

The latch can have a rounded end 216a and rounded corners 216b at the end of the latch. The end, corners, and edges of the latch can be relatively smooth. The smooth surface will not tear surgical gloves when the sheath and system unit are used.

Figure 15:
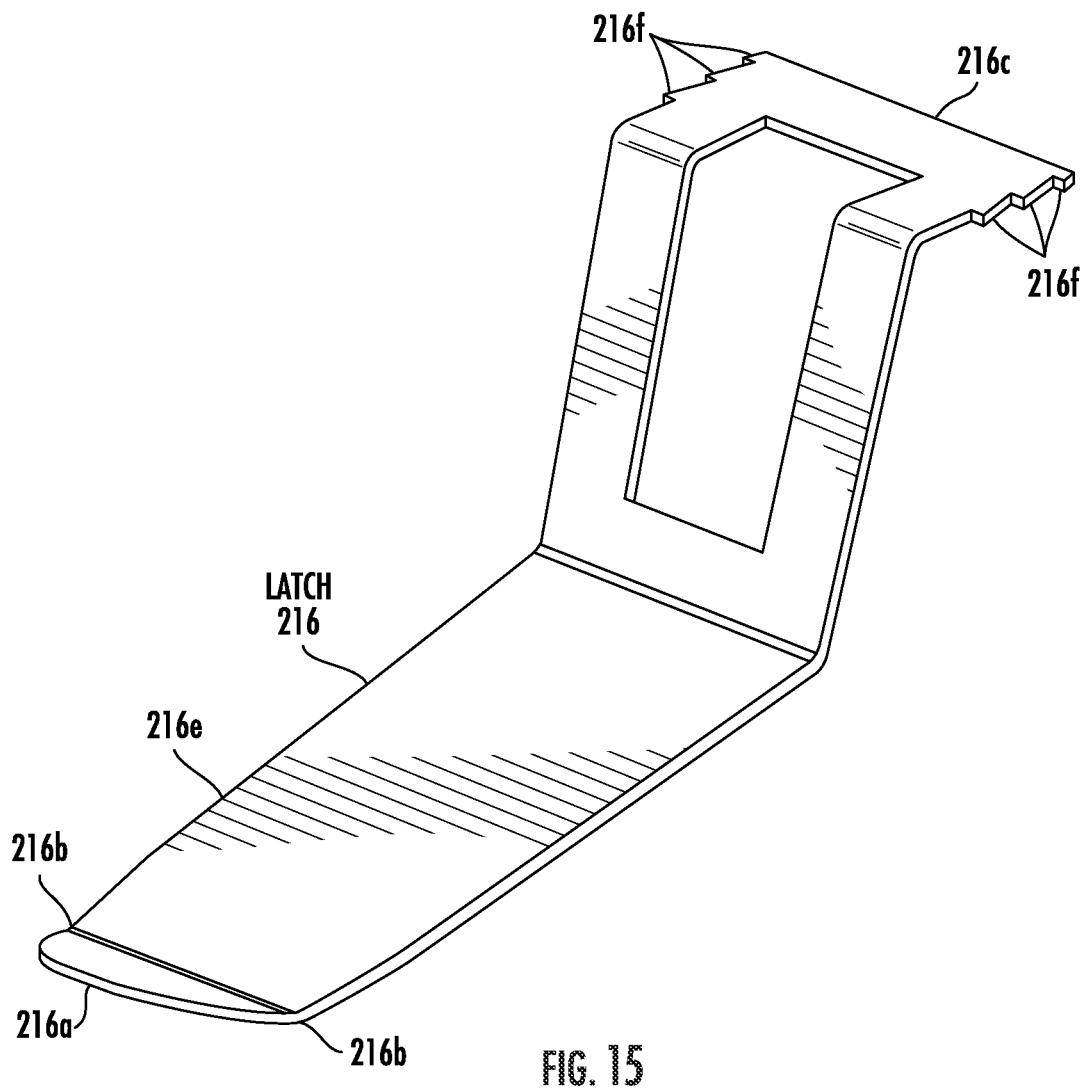
FIG. 15 shows a perspective view of the latch, in an implementation.

FIG. 15 shows a perspective view of the latch 216, in an implementation. The latch has a general "S" shape. The end 216c of the latch that is distally located with respect to the round end 216a of the latch has a number of extensions 216f (e.g., three triangular-shaped extensions or sawtooth-shaped extensions) that extend along the sides of the latch. The end portion of the latch and the extension fit into a pocket 1460 of the lid. The extensions dig into opposite sides of the pocket of the lid to hold the latch in the pocket.

The body of the sheath includes a first latch recess 1470 and a second latch recess 1475. When the latch is latched to the body, the bend 216d of the latch is positioned in the first latch recess and the tongue 216e of the latch is positioned in the second latch recess. The end of the latch 216 extends away from the body so that a user can engage this portion of the latch to open the latch from being latched.

In an implementation, the body includes a recess wall 1476 that partially surrounds both the first and second latch recesses. A portion of lip 235 that is adjacent to the first and second recesses may be a wall of the first and second recess latches. Wall 1476 may have a tapered shape with a first height at the tip tapering to a second height at a distal end of the wall that is distal from a portion of the lip where the recess wall attaches. The first height of the wall may be about 1 millimeter to about 15 millimeters. The second height of the wall may be about 0.5 millimeters to about 10 millimeters. The taper of the wall forms the second latch recess that has the same or a similar taper shape as the recess wall. The second recess can be deeper adjacent to the lip than at the distal end of the recess wall.

The wall may have a rounded shape at the distal end of the wall. Wall portions between the distal end of the all and the lip may be relatively straight. The inside surface of the wall that faces the first and second latch recesses may have a shape that is complementary to the shape of the portion of the latch that is inside the wall when the latch is latched to the body. The wall prevents or inhibits the latch from being caught on the clothing of a user, a user's fingers, or other objects that can attach to a side of the latch and open the latch.

In an implementation, the first latch recess is formed in a latch structure 1477, which extends into the second recess. Latch structure 1477 may include a number of struts that connect to lip 235 and a bottom surface of the second latch recess. Each strut includes a recess that collectively form the first latch recess. An edge 216*d* of the latch can be positioned in (i.e., engage) the first latch recess when the latch is closed. The first latch recess holds edge 216*d* in this latch recess to hold the latch closed and as such holds the lid of the sheath closed against the o-ring and body of the sheath. The latch structure 1477 and the first latch recess are inside the second latch recess. In an implementation, the latch structure 1477 does not connect with the latch wall. In another implementation, the latch structure is connected to the latch wall.

Figure 16:
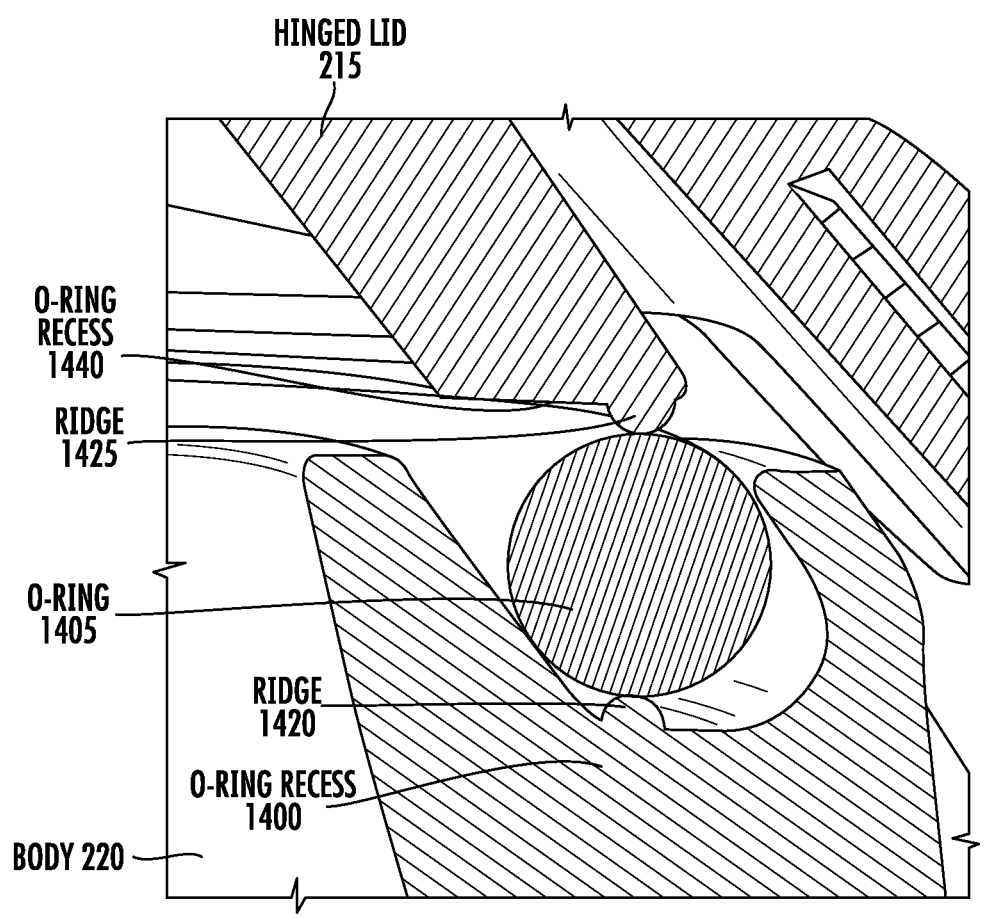
FIG. 16 shows a cross-sectional view of an upper portion of the sheath and shows a view between the lid and body where the O-ring is recessed the O-ring recess of the body of the sheath, in an implementation.

FIG. 16 shows a cross-sectional view of an upper portion of the sheath and shows a view between the lid and body where the O-ring is recessed the O-ring recess of the body of the sheath, in an implementation. The body includes a ridge 1420 that extends around the body in the O-ring recess 1400 of the body. The ridge is at a bottom area of the O-ring recess. The lid includes a ridge 1425 that extends around the lid in the O-ring recess 1440 of the lid. Each of the ridges can have a half-round shape or another shape. Each ridge may have a height of about 0.25 millimeters to about 3 millimeters. In an implementation, the height of each ridge is about 0.5 millimeters.

When the lid is closed against the body, and the latch is latched, the O-ring 1405 is compressed between the ridges. When the lid is closed, a line between the tops of the ridges may extend approximately through a center of the cross-section of the O-ring. The O-ring can have a diameter of about 0.5 millimeters to about 10 millimeters. The ridges compressing the O-ring create the seal the seals the sheath and seals the system unit inside the sheath.

The O-Ring is a deformable plastic type material. In an implementation, the O-ring is medical grade silicone rubber. The Shore durometer of the O-ring may be from about 8 A to about 22 A. In an implementation, the Shore durometer of the O-ring is 15+5 A. Shore durometer values are based on a unitless scale that ranges from 0 to 100. The Shore "A" durometers traditionally designates are typically used for softer materials and range broadly enough to cover flexible rubbers up to semi-rigid plastics with almost no flexibility. In contrast, Shore "D" durometers are typically used for harder materials, such as hard rubber, semi-rigid plastics and hard plastics. The deformable nature of the material that the O-ring is formed from facilitates the ridges 1420 and 1425 being able to form trenches in the O-ring when the O-ring is compressed allowing for a biological seal of the system unit in the sheath. In an implementation, a hermetic seal is formed. The O-ring may be translucent or clear silicone rubber so that the color of the O-ring is not a distracting during use.

Figure 17:
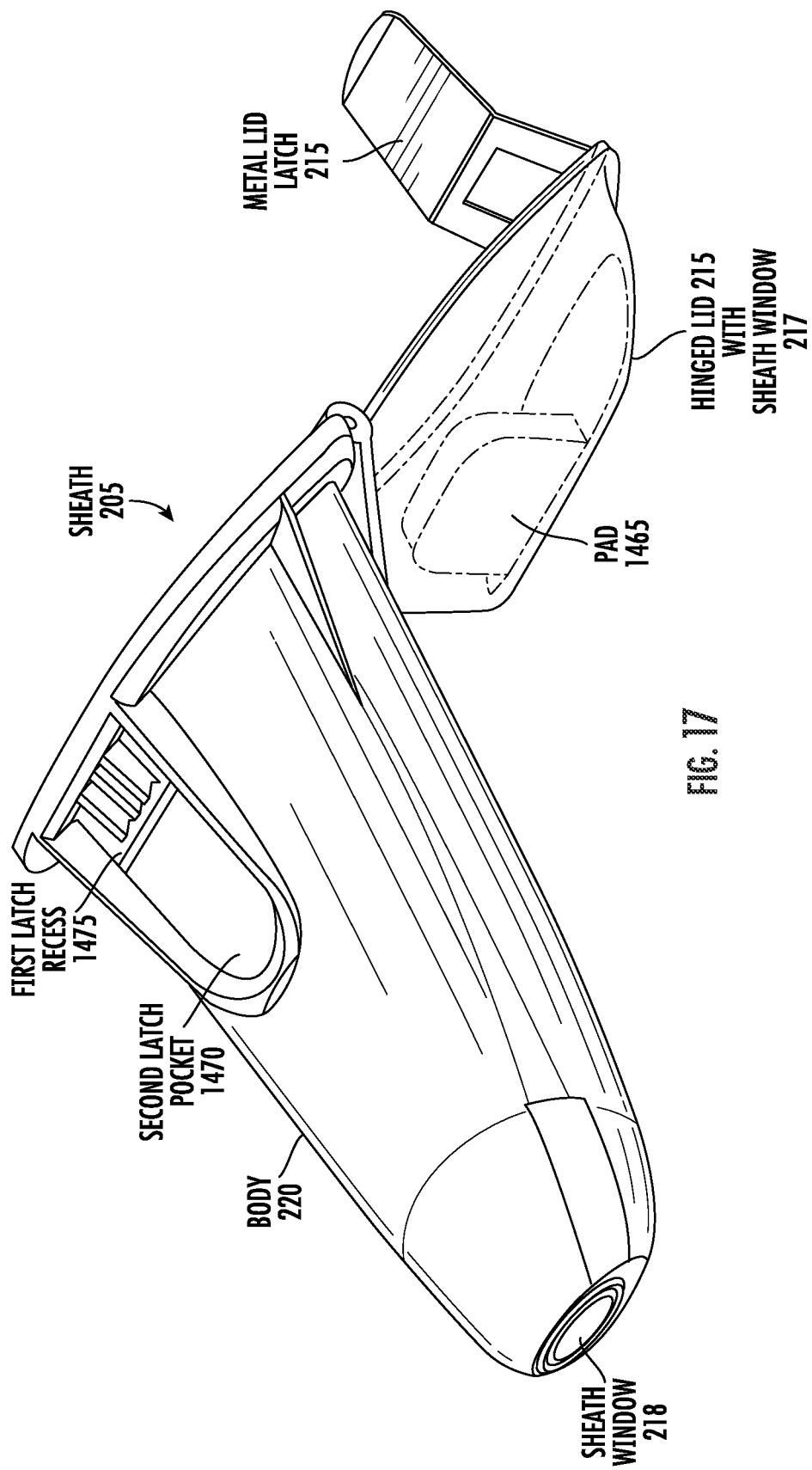
FIG. 17 shows a perspective view of the sheath, in an implementation.

FIG. 17 shows a perspective view of the sheath 205, in an implementation. The lid is shown in an open position with respect to the body where a system unit can be inserted into the sheath or removed from the sheath. The figure shows the second sheath window 218 at the bottom of the body of the sheath. The second sheath window may generally be round from an end view. In a specific implementation, the second sheath window is circular. The upper and lower surface of the second sheath window may be approximately parallel.

Figure 18:
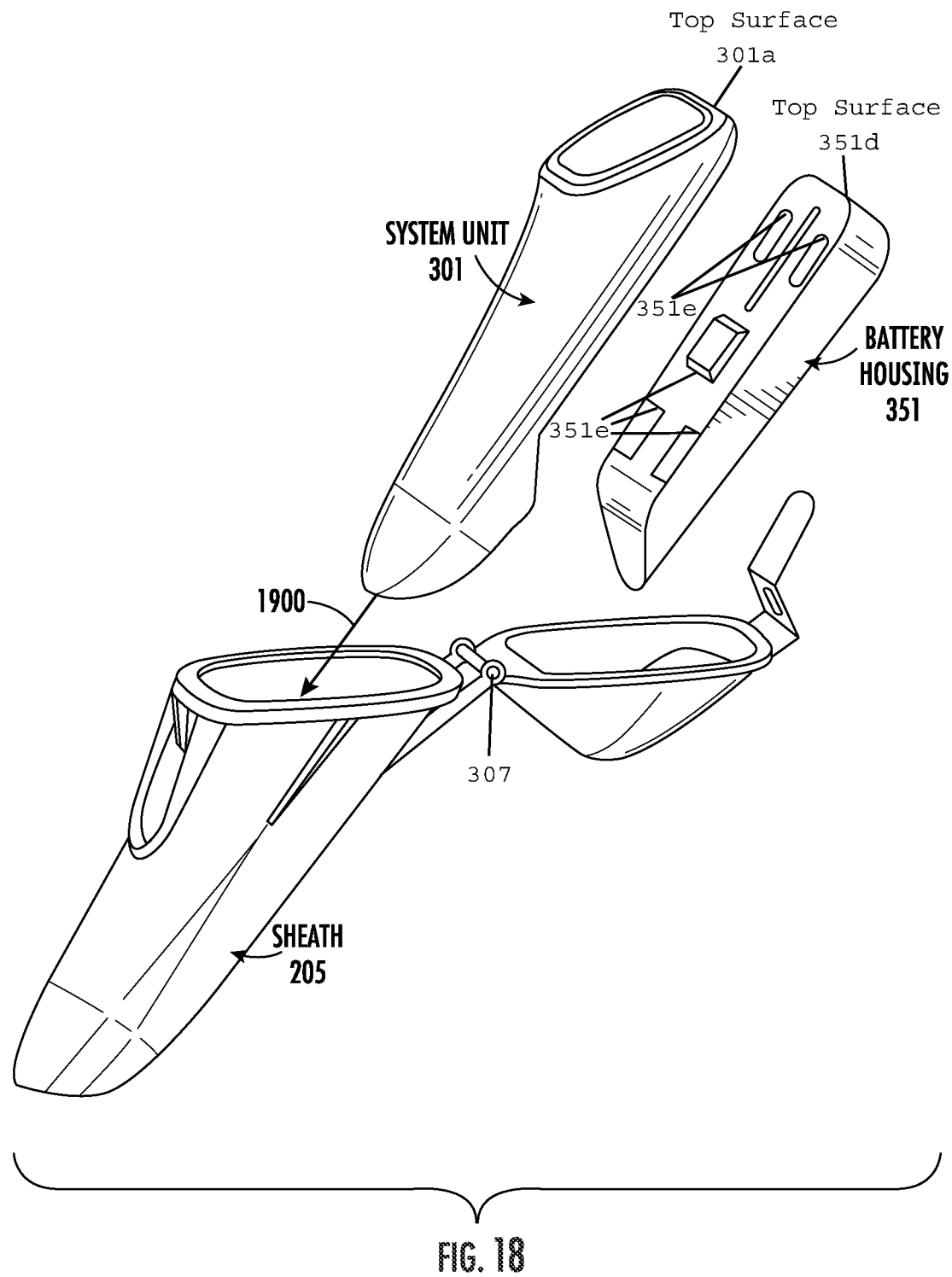
FIG. 18 shows a perspective view of the sheath, system unit, and power block, in an implementation.

FIG. 18 shows a perspective view of the sheath, system unit, and power block, in an implementation. The sheath is shown with the sheath lid open and the system unit above the opening of the body of the sheath. When the power block is placed onto the system unit, the system unit and power block may be placed into the sheath as indicated by arrow 1900. The lid may then be closed and the system unit and power block sealed in the sheath ready for use.

Figure 19:
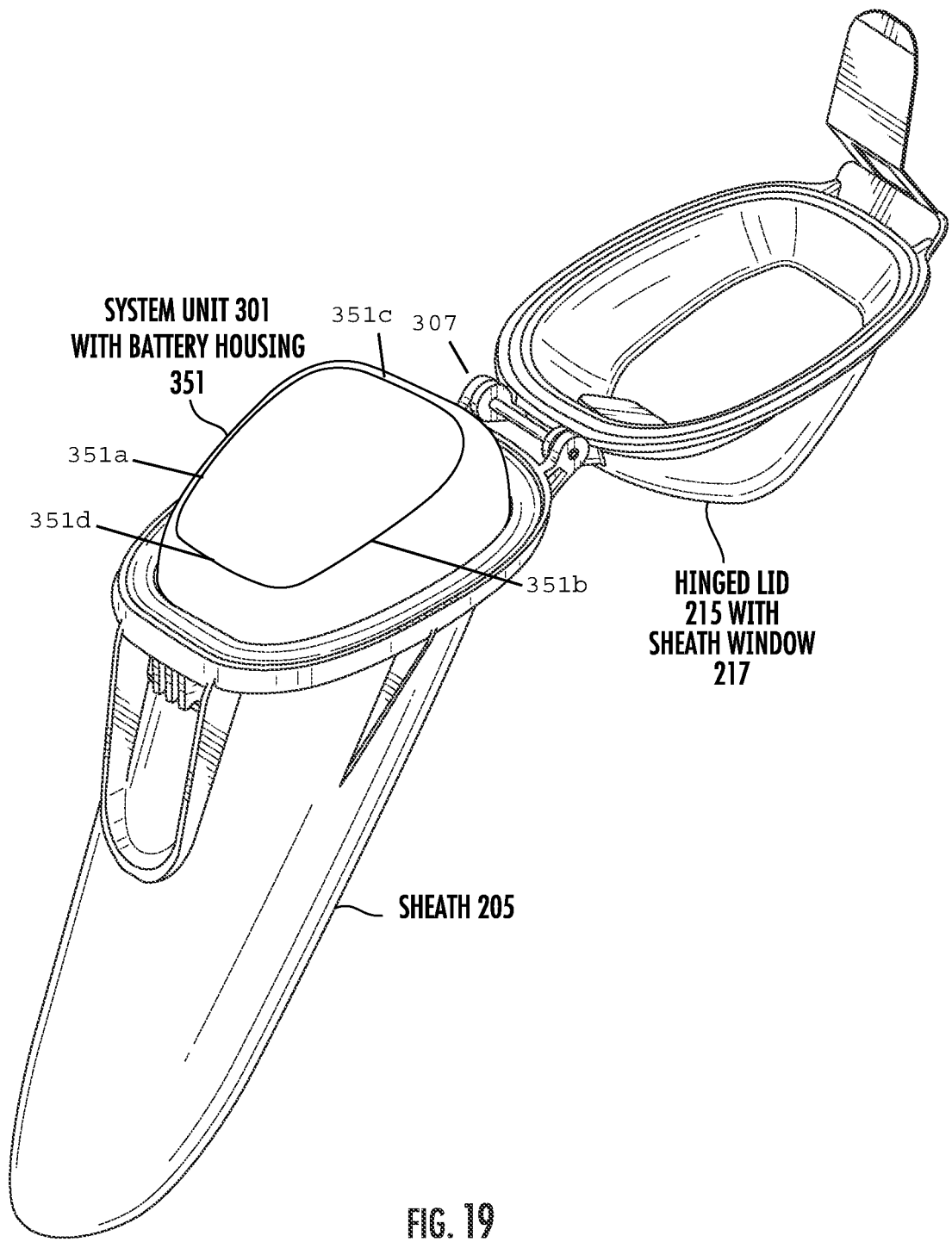
FIG. 19 shows a perspective view of the sheath, system unit, and power block, in an implementation with the lid of the sheath opened.

FIG. 19 shows a perspective view of the sheath, system unit, and power block, in an implementation. The sheath is shown with the sheath lid open, the latch unlatched, and the system unit with the power block attached is in the sheath. The O-ring 1405 is shown positioned in the O-ring recess 1400. When the lid is closed, the O-ring is pinched in the O-ring recess by the top and bottom ridges 1420 and 1425. The display of the system unit is outside of the body of the sheath as shown when the lid is open when the probe face of the probe tip of the system unit contacts the second window of the sheath.

FIG. 20 shows a perspective view of the sheath, system unit, and power block, in an implementation. The sheath is shown with the sheath lid closed, the latch latched, and the system unit with the power block attached is in the sheath. The ridges of the lid and body contact and pinch the O-ring to seal the system unit in the sheath. The display of the system unit is visible through the first window of the lid of the sheath. Information (e.g., text, graphics, or both) that is displayed on the display of the system unit is visible to a user looking through the second window of the lid. The display and window are both proximally located with the probe face and second window distally located when the system is ready for use. With the second window in contact with tissue, the display faces away from the tissue so that the display, through the first window, can be seen by a user.

The display has left-right symmetry. And the angle between the left side 351*a* and the right side 351*b* of the display approximately matches the angle between the left and right sides of the opening of the body of the sheath (FIG. 19). The angles are from about 5 degrees to about 45 degrees. The angles are a keying feature that allow the system unit to be placed completely in the sheath one way. In an implementation, the display and the opening of the body of the sheath do not have front back symmetry (e.g., for the sheath between the sides nearest the hinge and latch). In an implementation, one or more of the surfaces of the system unit and the sheath include mechanical keying features (e.g., slot and tabs) that allow the system unit to be placed in the sheath in only one orientation.

In an implementation, information is displayed on the display in an orientation where the text or other information is arranged for reading from left to right (e.g., from side 315*a* to side 351*b*) where the text is upright with the top of text (e.g., tops letters) nearest to side 315*c* and the bottom of text (e.g., bottoms of letters) nearest to side 351*d*.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:
1. A method comprising:
forming a housing for an oximeter device, wherein the housing comprises; sidewall and a bezel located on the sidewall, the sidewall comprises a first opening, the bezel comprises a second opening that is aligned with the first opening, and the bezel has a first height from the sidewall of the housing;

positioning an aperture plate in the second opening of the bezel;

positioning at least a portion of a printed circuit board (PCB) in the second opening of the bezel and in the first opening of the sidewall, wherein the PCB is coupled to the aperture plate inside the second opening and a plurality of detectors are located on a first surface of the PCB inside the second opening;

flowing epoxy over the aperture plate and through apertures formed in the aperture plate to the detectors and PCB; and polishing the epoxy and bezel to form a probe face of the oximeter device.

2. The method of claim 1 wherein the probe face is flush with a surface of the sidewall of the housing.

3. The method of claim 1 wherein the probe face is above a surface of the sidewall of the housing.

4. The method of claim 3 wherein the probe face is flush with a surface of the bezel.

5. The method of claim 1 wherein flowing the epoxy includes flowing the epoxy between a sidewall of the PCB and a sidewall of the second opening.

6. The method of claim 1 wherein flowing the epoxy includes flowing the epoxy between a sidewall of the PCB and a sidewall of the first opening, and flowing the epoxy between the sidewall of the PCB and a sidewall of the second opening.

7. The method of claim 1 comprising positioning a plurality of spacers between the first surface of the PCB and a surface of the aperture plate.

8. The method of claim 1 wherein the detectors are photodetectors.

9. The method of claim 1 wherein the sidewall comprises a first end and a second end, the first end is proximally located to the first opening of the housing and the second end is distally located from the first opening of the housing, and the aperture plate is nearer the second end than the first end.

10. The method of claim 9 wherein each of the detectors is registered with one of the apertures on the aperture plate, such that light entering the apertures is detectable by the detectors.

11. The method of claim 1 comprising:
coupling a plurality of spacers to a surface of the printed circuit board that faces the aperture plate; and
coupling the spacers to a surface of the aperture plate that faces the printed circuit board.

12. The method of claim 1 wherein the polishing removes a portion of the epoxy and a portion of the bezel, after the polishing the bezel has a second height from the sidewall of the housing, and the second height is less than the first height.

13. A method comprising:
forming a housing for an oximeter device, wherein the housing comprises; a sidewall and a bezel extending from the sidewall of the housing, the sidewall comprises a first opening, the bezel comprises a second opening that is aligned with the first opening, and the bezel has a first height from the sidewall of the housing;
positioning an aperture plate in the second opening of the bezel;
positioning at least a portion of a printed circuit board (PCB) in the second opening of the bezel and in the first opening of the sidewall, wherein the PCB is coupled to the aperture plate inside the second opening and a plurality of photodetectors are located on a first surface of the PCB inside the second opening and aligned with apertures of the aperture plate;
flowing epoxy over the aperture plate and through the apertures formed in the aperture plate to the photodetectors and PCB; and
polishing the epoxy and bezel to form a probe face of the oximeter device.

14. The method of claim 13 wherein the probe face is flush with a surface of the sidewall of the housing.

15. The method of claim 13 wherein the probe face is above a surface of the sidewall of the housing.

16. The method of claim 15 wherein the probe face is flush with a surface of the bezel.

17. The method of claim 13 wherein flowing the epoxy includes flowing the epoxy between a sidewall of the PCB and a sidewall of the second opening.

18. The method of claim 13 wherein flowing the epoxy includes flowing the epoxy between a sidewall of the PCB and a sidewall of the first opening, and flowing the epoxy between the sidewall of the PCB and a sidewall of the second opening.

19. The method of claim 13 comprising positioning a plurality of spacers between a first surface of the PCB and a surface of the aperture plate.

20. The method of claim 13 wherein the sidewall comprises a first end and a second end, the first end is proximally located to the first opening of the housing and the second end is distally located from the first opening of the housing, and the aperture plate is nearer the second end than the first end.

21. The method of claim 20 wherein each of the detectors is registered with one of the apertures on the aperture plate, such that light entering the apertures is detectable by the detectors.

22. The method of claim 13 comprising:
coupling a plurality of spacers to a surface of the printed circuit board that faces the aperture plate; and
coupling the spacers to a surface of the aperture plate that faces the printed circuit board.

23. The method of claim 13 wherein the polishing removes a portion of the epoxy and a portion of the bezel, after the polishing the bezel has a second height from the sidewall of the housing, and the second height is less than the first height.

24. A device comprising:
a housing comprising a processor located in the housing and a bottom wall, wherein an opening is formed in the bottom wall;
a portion of a printed circuit board located in the opening;
an aperture plate located in the opening, comprising a plurality of apertures;
a plurality of spacers coupled to a surface of the printed circuit board that faces the aperture plate and coupled to a surface of the aperture plate that faces the printed circuit board;
a source structure located in the opening;
a plurality of photodetectors formed on the surface of the printed circuit board and registered with the apertures, wherein the photodetectors are coupled to the processor; and
an epoxy material located over a surface of the aperture plate that faces away from the printed circuit board, wherein the device is an oximeter.

25. The device of claim 24 wherein the epoxy is located in the apertures of the aperture plate.

26. The device of claim 24 wherein the epoxy is located in a space between the aperture plate and the printed circuit board.

27. The device of claim 24 wherein the epoxy is located between a sidewall of the opening and a portion of a sidewall of the printed circuit board located in the opening.

28. The device of claim 24 wherein a portion of the photodetectors is located in the apertures of the aperture plate.

29. The device of claim 24 wherein the photodetectors are located below the surface of the aperture plate that faces the printed circuit board.

* * * * *